(12) United States Patent
Butt et al.

(10) Patent No.: US 10,435,727 B2
(45) Date of Patent: Oct. 8, 2019

(54) ISOLATED CODON OPTIMIZED NUCLEIC ACID

(71) Applicants: Sher Ali Butt, San Diego, CA (US); Jacob Michael Vogan, Oakland, CA (US)

(72) Inventors: Sher Ali Butt, San Diego, CA (US); Jacob Michael Vogan, Oakland, CA (US)

( * ) Notice: Subject to any disclaimer, the term of this patent is extended or adjusted under 35 U.S.C. 154(b) by 0 days.

(21) Appl. No.: 15/719,430

(22) Filed: Sep. 28, 2017

(65) Prior Publication Data

US 2018/0155748 A1 Jun. 7, 2018

Related U.S. Application Data

(63) Continuation of application No. 15/096,164, filed on Apr. 11, 2016, now abandoned.

(60) Provisional application No. 62/145,430, filed on Apr. 9, 2015.

(51) Int. Cl.
| | | |
|---|---|---|
| *C12P 13/02* | (2006.01) | |
| *C12P 17/06* | (2006.01) | |
| *C12P 7/22* | (2006.01) | |
| *C12N 15/52* | (2006.01) | |
| *C12P 7/42* | (2006.01) | |

(52) U.S. Cl.
CPC ............. *C12P 13/02* (2013.01); *C12N 15/52* (2013.01); *C12P 7/22* (2013.01); *C12P 7/42* (2013.01); *C12P 17/06* (2013.01)

(58) Field of Classification Search
None
See application file for complete search history.

(56) References Cited

U.S. PATENT DOCUMENTS

| | | |
|---|---|---|
| 6,630,507 B1 | 10/2003 | Hampson |
| 7,179,800 B2 | 2/2007 | Martin |
| 8,884,100 B2 | 11/2014 | Page |
| 9,394,510 B2 | 7/2016 | Peet |
| 9,822,384 B2 | 11/2017 | Poulos |
| 2007/0032544 A1 | 2/2007 | Korthout |
| 2008/0031977 A1 | 2/2008 | Musty |
| 2009/0042964 A1 | 2/2009 | Malamas |
| 2009/0042974 A1 | 2/2009 | Parker |
| 2010/0016418 A1 | 1/2010 | Guy |
| 2010/0292345 A1 | 11/2010 | Pertwee |
| 2011/0021617 A1 | 1/2011 | Korthout |
| 2011/0098348 A1 | 4/2011 | DeMeijer |
| 2012/0144523 A1 | 6/2012 | Page |
| 2015/0128301 A1 | 5/2015 | Page |
| 2016/0010126 A1 | 1/2016 | Poulos |

FOREIGN PATENT DOCUMENTS

| | | |
|---|---|---|
| WO | WO2011017798 A1 | 2/2011 |
| WO | WO2016010827 A1 | 1/2016 |

OTHER PUBLICATIONS

Taura, F., Studies on tetrahydrocannabinolic acid synthase that produces the acidic precursor of tetrahydrocannabinol, the pharmacologically active cannabinoid in marajuana, Drug Discover Ther. 2009: 3(3): 83-87.
Taura, F., et al.. Purification and characterization of cannabidiolic-acid synthase from *Cannabis sativa* L., The Journal of Biological Chemistry, vol. 271, No. 29, Issue of Jul. 19, pp. 17411-17416, 1996.
Taura, F. el al., Cannabidiolic-acid synthase the chernotype-determining enzyme in the fiber-type Cannabis sativa, FEBS Letters 581 (2007) 2929-2934.
Fellermeier, M., et al., Biosynthesis of cannabinoids. Incorporation experiments with 13C-labeled glucose, Eur. J. Biochem. 268, 1596-1604 (2001).
Fellermeier, M. and Zenk, M.H., Prenylation of olivetolate by a hemp transferase yields cannabigerolic acid, the precursor of tetrahydrocannabinol, FEBS Letters 427 (1998) 283-285.
Nevoigt, E., Progress in metabolic enoineering of *Saccharomyces cerevisiae*, Microbiology and Molecular Biology Reviews, Sep. 2008, p. 379-412, vol. 72, No. 3.
Flores-Sanchez, I.J. and Verpoorte, R., Secondary metabolism in cannabis, Phytochem. Rev. (2008) 7:615-639. DOI 10.1007/s11101-008-90994-4.
Eisenreich, W., et al., The deoxyxylulose phosphate pathway of terpenoid biosynthesis in plants and microorganisms, Chemistry & Biology, Sep. 1998, 5:R221-R233.
Gagne, S.J., et al.. Identification of olivetolic acid cyclase from Cannabis sativa reveals a unique catalytic route to plant polyketides, PNAS, Jul. 31, 2012, vol. 109, No. 31, pp. 12811-12816.

*Primary Examiner* — Hope A Robinson

(57) ABSTRACT

The present invention is a method for the biosynthesis of hundreds of compounds, mainly found in the *Cannabis* plant. The starting material for these compounds can be any biological compound that is used/produced in a biological organism from the sugar family starting materials or other low cost raw materials processed via enzymes or within organisms to give final products. These final products include, but are not limited to: cannabinoids, terpenoids, stilbenoids, flavonoids, phenolic amides, lignanamides, spermidine alkaloids, and phenylpropanoids. Specifically, the present invention relates to the regular/modified/synthetic gene(s) of select enzymes are processed and inserted into an expression system (vector, cosmid, BAC, YAC, phage, etc.) to produce modified hosts. The modified host is then optimized for efficient production and yield via manipulation, silencing, and amplifying inserted or other genes in the host, leading to an efficient system for product.

1 Claim, 8 Drawing Sheets

Specification includes a Sequence Listing.

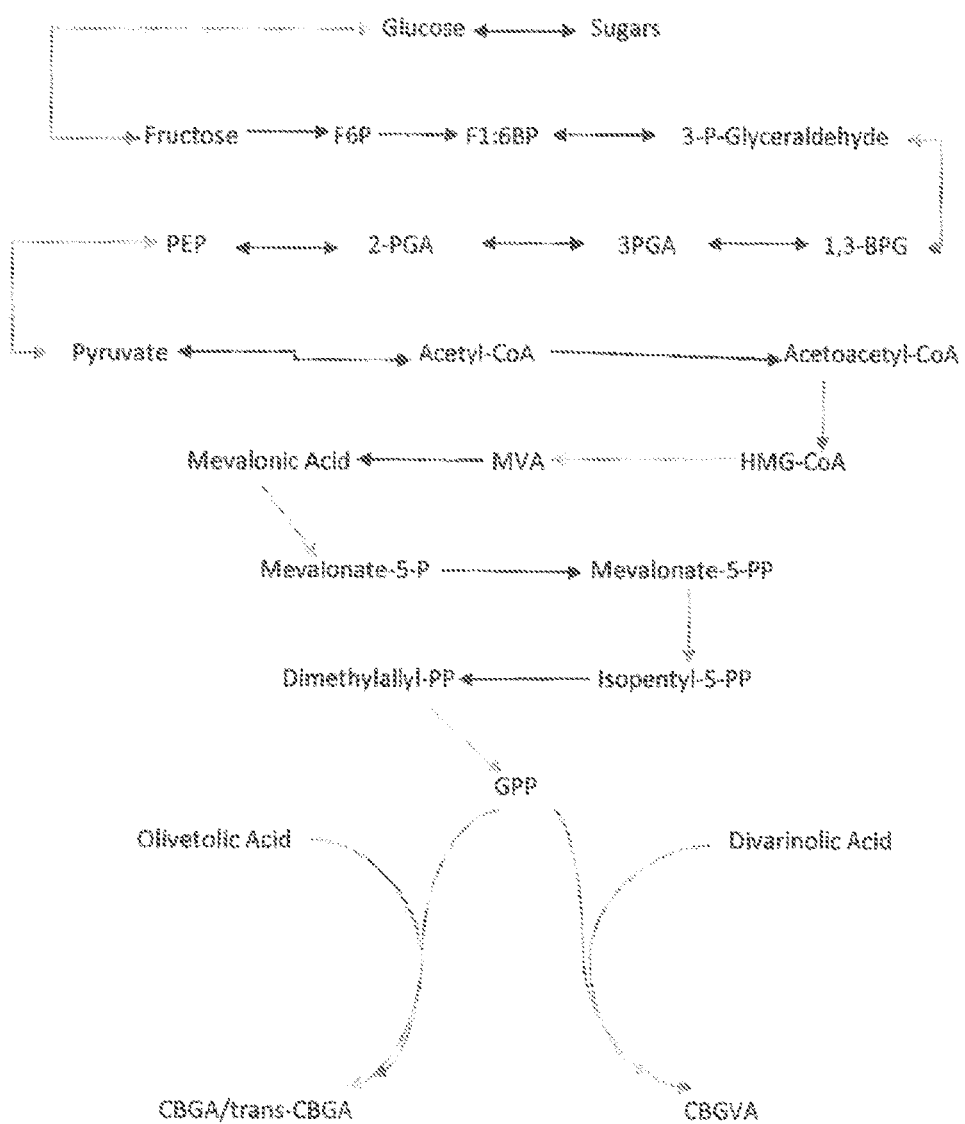
Figure 1 (General Pathway Scheme)

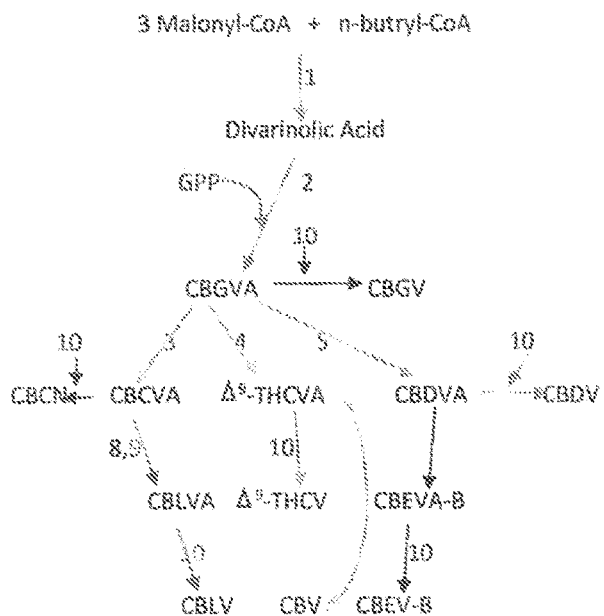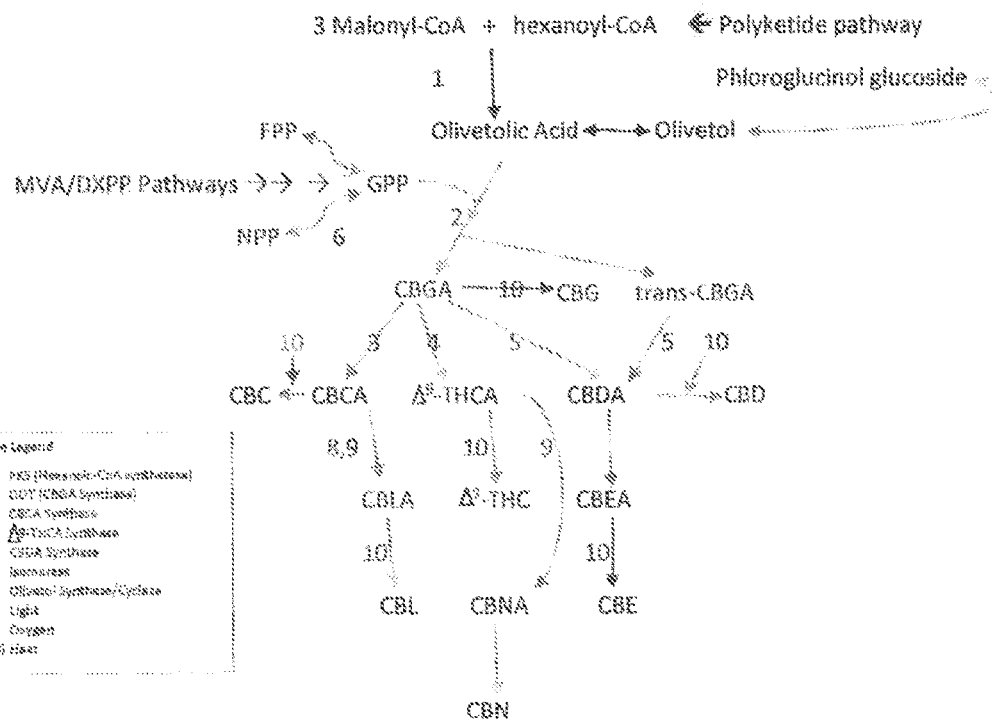
Figure 2 (27 Cannabinoids)

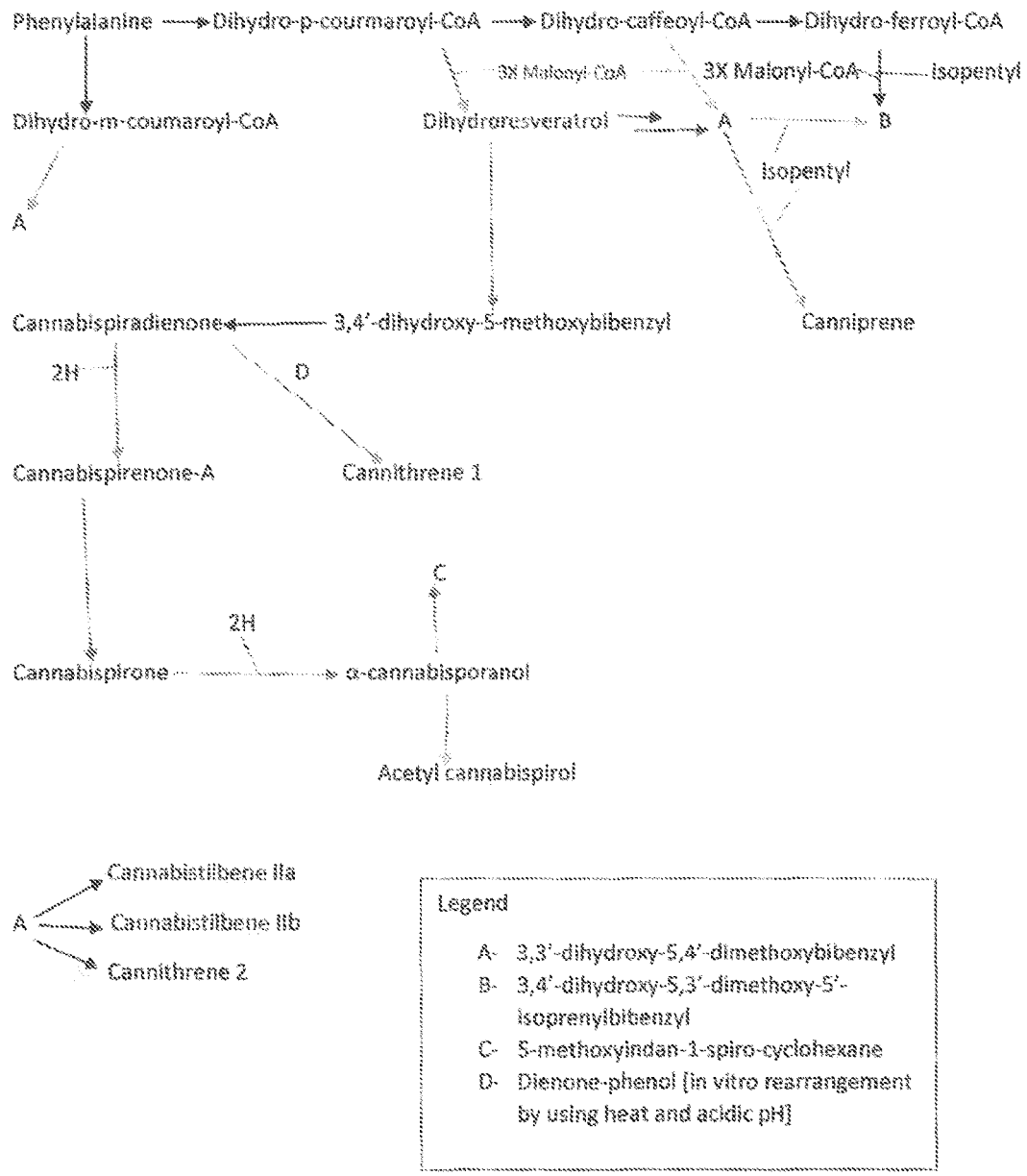
Figure 3 (Stilbenoids)

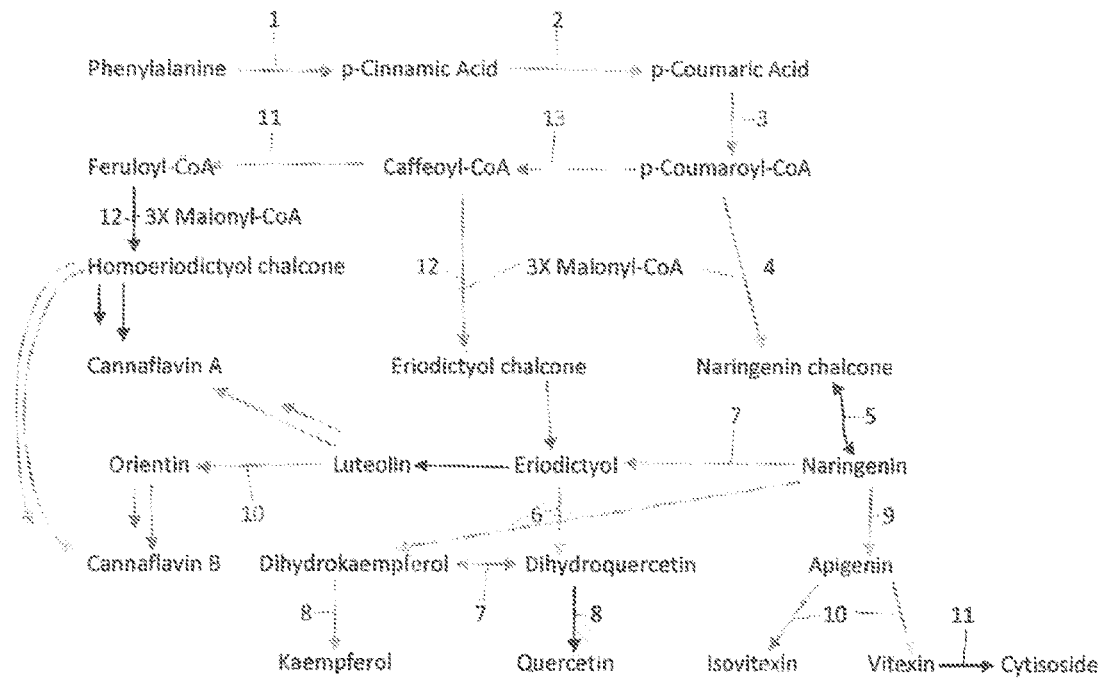

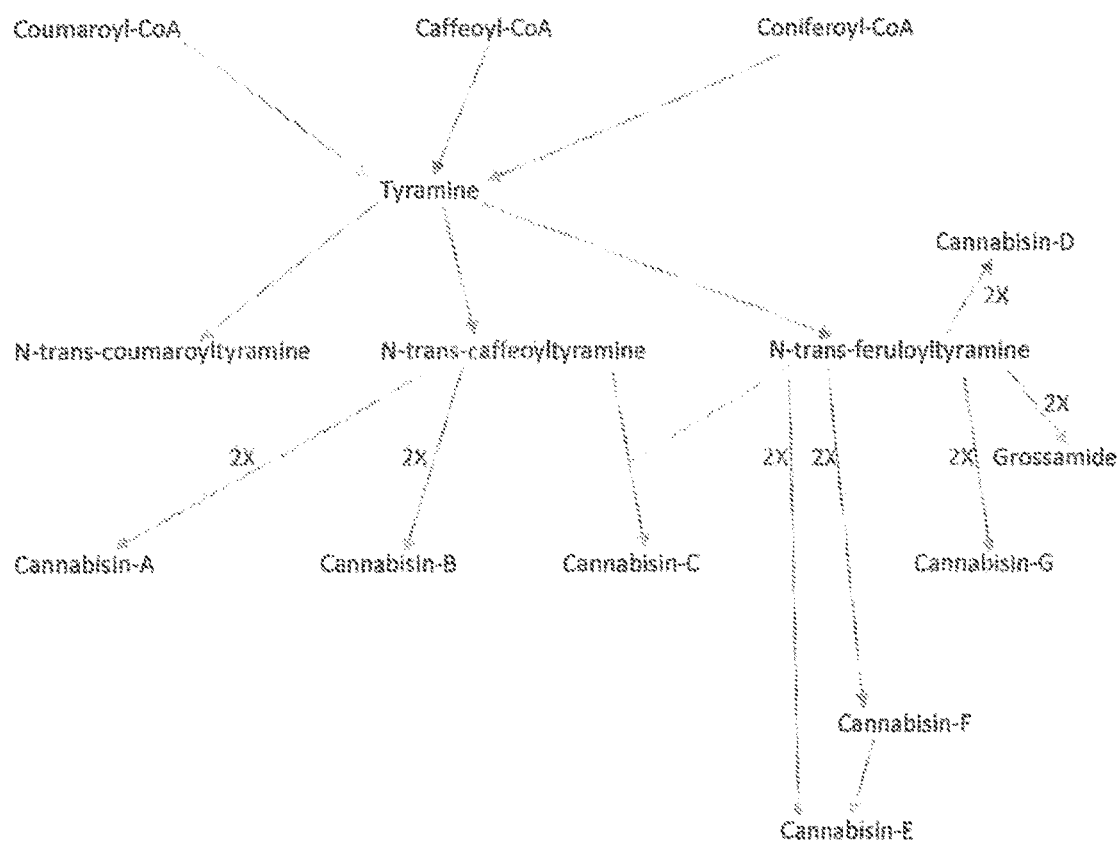

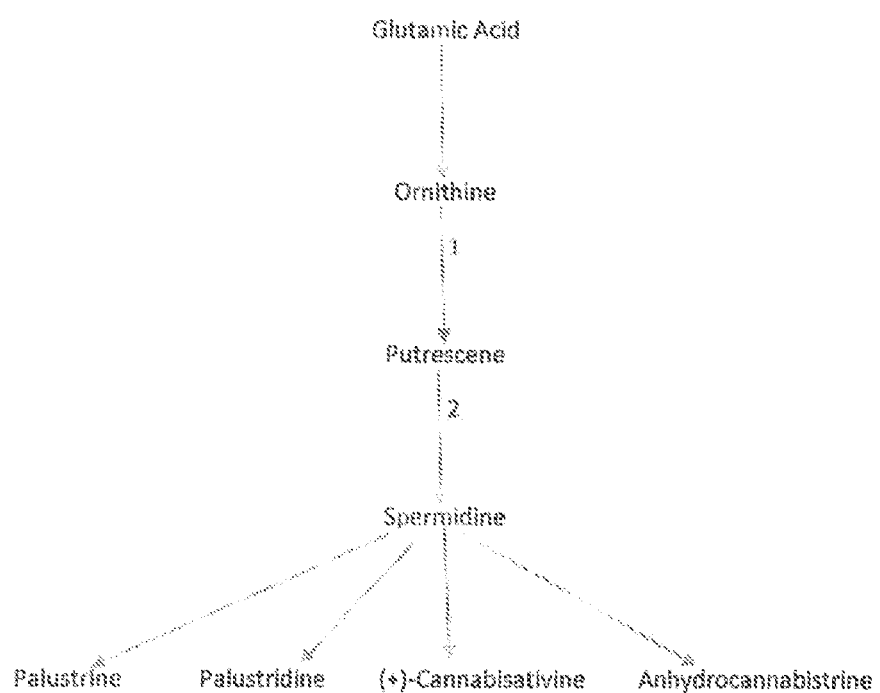

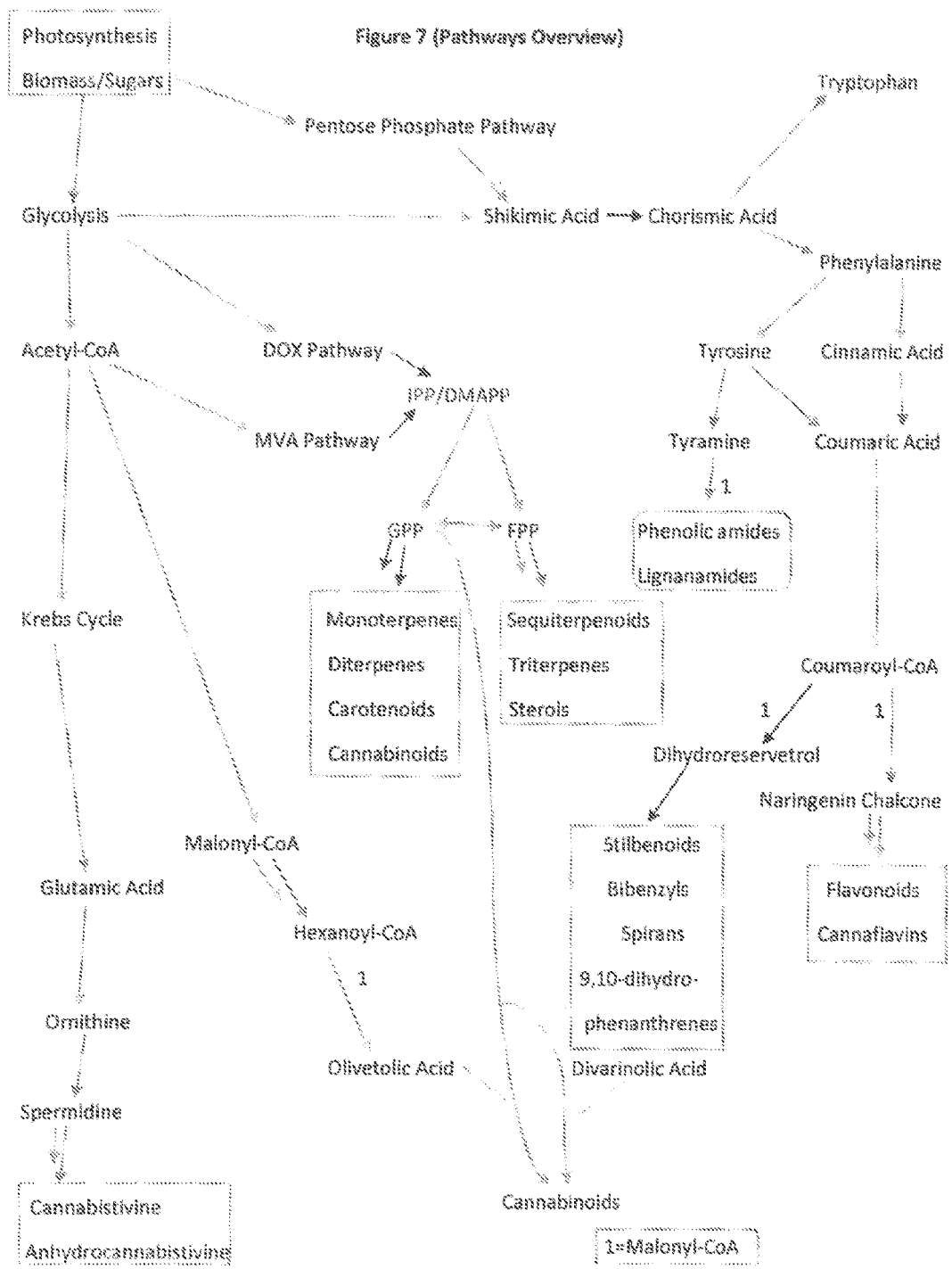

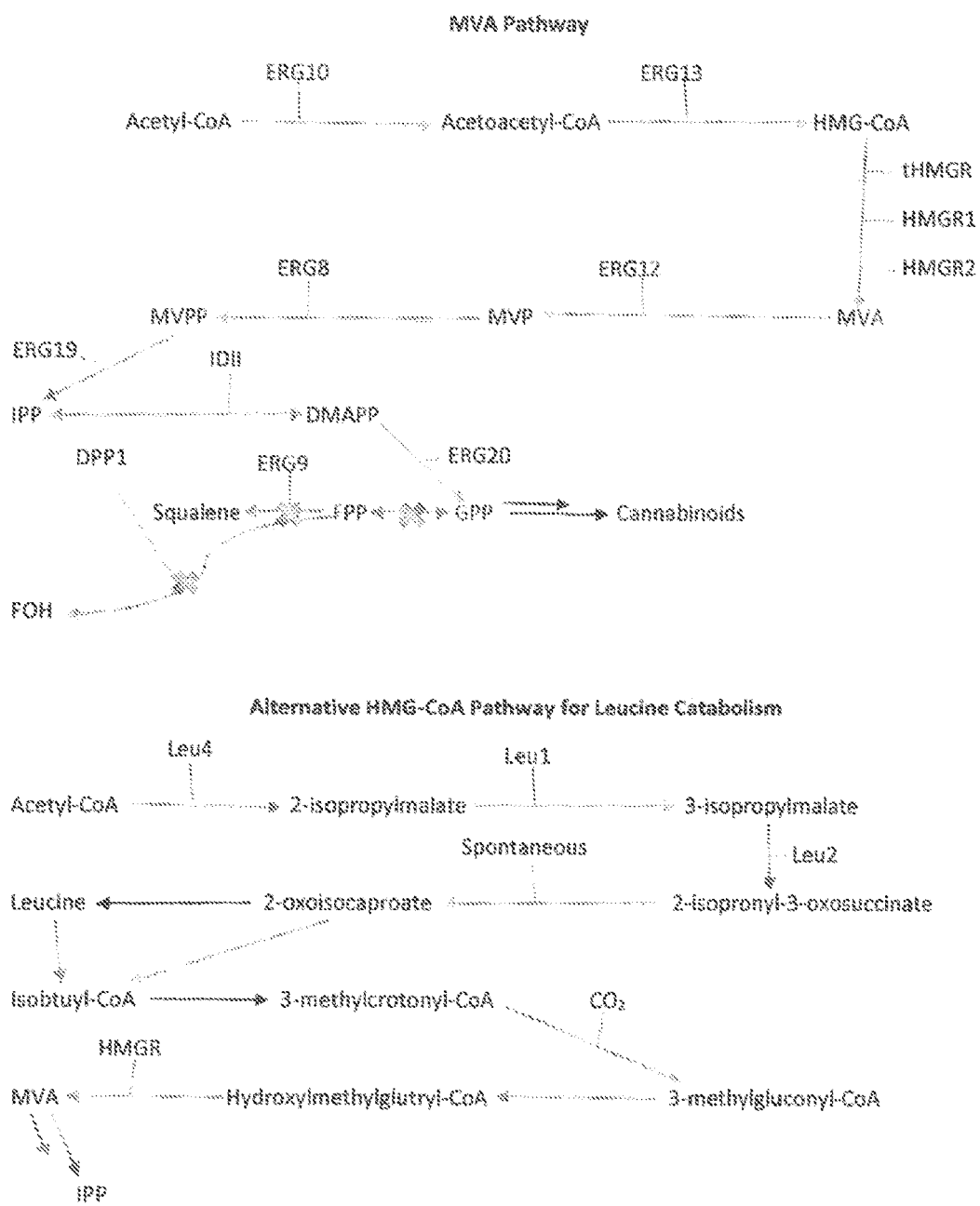
Figure 8 (Genetic Modifications of genes in our pathway for accelerated high yield development)

SEQUENCE LISTING

<160> NUMBER OF SEQ ID NOS: 36

<210> SEQ ID NO 1
<211> LENGTH: 60
<212> TYPE: DNA
<213> ORGANISM: Artificial Sequence
<220> FEATURE:
<223> OTHER INFORMATION: Synthetic: ERG9pS1

<400> SEQUENCE: 1
gtacatttca tagcccatct tcaacaacaa taccgactta cccgtacgct gcaggtcgac     60

<210> SEQ ID NO 2
<211> LENGTH: 60
<212> TYPE: DNA
<213> ORGANISM: Artificial Sequence
<220> FEATURE:
<223> OTHER INFORMATION: Synthetic: ERG9 250dwS2

<400> SEQUENCE: 2
cagattgacg gagagagggc cacattgttt gtcggcaata aatcgatgaa ttcgagctcg     60

<210> SEQ ID NO 3
<211> LENGTH: 22
<212> TYPE: DNA
<213> ORGANISM: Artificial Sequence
<220> FEATURE:
<223> OTHER INFORMATION: Synthetic: Hph F

<400> SEQUENCE: 3
atgggtaaaa agcctgaact ca     22

<210> SEQ ID NO 4
<211> LENGTH: 23
<212> TYPE: DNA
<213> ORGANISM: Artificial Sequence
<220> FEATURE:
<223> OTHER INFORMATION: Synthetic: Hph R

<400> SEQUENCE: 4
ttattccttt gccctcggac gag     23

<210> SEQ ID NO 5
<211> LENGTH: 22
<212> TYPE: DNA
<213> ORGANISM: Artificial Sequence
<220> FEATURE:
<223> OTHER INFORMATION: Synthetic: ERG9 450dwR

<400> SEQUENCE: 5
agatgctagt caatggcaga ag                                    22

<210> SEQ ID NO 6
<211> LENGTH: 22
<212> TYPE: DNA
<213> ORGANISM: Artificial Sequence
<220> FEATURE:
<223> OTHER INFORMATION: Synthetic: ERG9p300upF

<400> SEQUENCE: 6
tgcttacaca gagtgaacct gc                                    22

<210> SEQ ID NO 7
<211> LENGTH: 19
<212> TYPE: DNA
<213> ORGANISM: Artificial Sequence
<220> FEATURE:
<223> OTHER INFORMATION: Synthetic: ERG9 300R

<400> SEQUENCE: 7
ctcgtggaag tgacgcaac                                        19

<210> SEQ ID NO 8
<211> LENGTH: 32
<212> TYPE: DNA
<213> ORGANISM: Artificial Sequence
<220> FEATURE:
<223> OTHER INFORMATION: Synthetic: pGPD-BamHI F

<400> SEQUENCE: 8
cgggatccag tttatcatta tcaatactcg cc                         32

<210> SEQ ID NO 9
<211> LENGTH: 31
<212> TYPE: DNA
<213> ORGANISM: Artificial Sequence
<220> FEATURE:
<223> OTHER INFORMATION: Synthetic: pGPD-NotIR

<400> SEQUENCE: 9
ggggcggccg cgagctcagt ttatcattat c                          31

<210> SEQ ID NO 10
<211> LENGTH: 42
<212> TYPE: DNA
<213> ORGANISM: Artificial Sequence
<220> FEATURE:
<223> OTHER INFORMATION: Synthetic: tHMGR-NotIF

<400> SEQUENCE: 10
ggggcggccg caaaacaatg ttgtcacgac ttttccgtat gc              42

<210> SEQ ID NO 11
<211> LENGTH: 37
<212> TYPE: DNA
<213> ORGANISM: Artificial Sequence
<220> FEATURE:

<223> OTHER INFORMATION: Synthetic: tHMGR-SpeIR

<400> SEQUENCE: 11
gactagttca agctgacttc ttggtgcacg ttccttg    37

<210> SEQ ID NO 12
<211> LENGTH: 25
<212> TYPE: DNA
<213> ORGANISM: Artificial Sequence
<220> FEATURE:
<223> OTHER INFORMATION: Synthetic: ERG1F

<400> SEQUENCE: 12
atgtctgctg ttaacgttgc acctg    25

<210> SEQ ID NO 13
<211> LENGTH: 22
<212> TYPE: DNA
<213> ORGANISM: Artificial Sequence
<220> FEATURE:
<223> OTHER INFORMATION: Synthetic: ERG1R

<400> SEQUENCE: 13
ttaaccaatc aactcaccaa ac    22

<210> SEQ ID NO 14
<211> LENGTH: 38
<212> TYPE: DNA
<213> ORGANISM: Artificial Sequence
<220> FEATURE:
<223> OTHER INFORMATION: Synthetic: ERG1-split F

<400> SEQUENCE: 14
cgggatccct cgagttgttc gctgctgaca gcgataac    38

<210> SEQ ID NO 15
<211> LENGTH: 44
<212> TYPE: DNA
<213> ORGANISM: Artificial Sequence
<220> FEATURE:
<223> OTHER INFORMATION: Synthetic: ERG1-splitR

<400> SEQUENCE: 15
cgggatccgc tagcggtacc acatgggtcc tttatattga cacg    44

<210> SEQ ID NO 16
<211> LENGTH: 23
<212> TYPE: DNA
<213> ORGANISM: Artificial Sequence
<220> FEATURE:
<223> OTHER INFORMATION: Synthetic: ERG1 90up F

<400> SEQUENCE: 16
atcagaacaa ttgtccagta ttg    23

<210> SEQ ID NO 17
<211> LENGTH: 21
<212> TYPE: DNA
<213> ORGANISM: Artificial Sequence
<220> FEATURE:
<223> OTHER INFORMATION: Synthetic: ERG1100dwR

<400> SEQUENCE: 17
aatgtactat acaagccttc c    21

```
<210> SEQ ID NO 18
<211> LENGTH: 40
<212> TYPE: DNA
<213> ORGANISM: Artificial Sequence
<220> FEATURE:
<223> OTHER INFORMATION: Synthetic: bSQS-NotIF

<400> SEQUENCE: 18
ggggcggccg caaaacaatg gggatgcttc gctggggagt                               40

<210> SEQ ID NO 19
<211> LENGTH: 31
<212> TYPE: DNA
<213> ORGANISM: Artificial Sequence
<220> FEATURE:
<223> OTHER INFORMATION: Synthetic: bSQS-SpeIR

<400> SEQUENCE: 19
gactagttta gctcctcaat cgtcaaagg t                                        31

<210> SEQ ID NO 20
<211> LENGTH: 42
<212> TYPE: DNA
<213> ORGANISM: Artificial Sequence
<220> FEATURE:
<223> OTHER INFORMATION: Synthetic: Cre-NotIF

<400> SEQUENCE: 20
ggggcggccg caaaacaatg gacatgttca gggatcgcca gg                           42

<210> SEQ ID NO 21
<211> LENGTH: 31
<212> TYPE: DNA
<213> ORGANISM: Artificial Sequence
<220> FEATURE:
<223> OTHER INFORMATION: Synthetic: Cre-SpeIR

<400> SEQUENCE: 21
gactagtcta atcgccatct tccagcaggc g                                       31

<210> SEQ ID NO 22
<211> LENGTH: 60
<212> TYPE: DNA
<213> ORGANISM: Artificial Sequence
<220> FEATURE:
<223> OTHER INFORMATION: Synthetic: Padh-Loxp-BamHIF

<400> SEQUENCE: 22
cgggatccat aacttcgtat agcatacatt atacgaagtt atgtggaata tttcggatat        60

<210> SEQ ID NO 23
<211> LENGTH: 56
<212> TYPE: DNA
<213> ORGANISM: Artificial Sequence
<220> FEATURE:
<223> OTHER INFORMATION: Synthetic: Padh-Kanmx4F

<400> SEQUENCE: 23
gcatacaatc aactaagcta agctaaaaca atgggtaagg aaaagactca cgtttc            56

<210> SEQ ID NO 24
<211> LENGTH: 56
<212> TYPE: DNA
<213> ORGANISM: Artificial Sequence
<220> FEATURE:
<223> OTHER INFORMATION: Synthetic: Padh-Kanmx4R
```

<400> SEQUENCE: 24
gaaacgtgag tcttttcctt acccattgtt ttagcttagc ttagttgatt gtatgc                56

<210> SEQ ID NO 25
<211> LENGTH: 53
<212> TYPE: DNA
<213> ORGANISM: Artificial Sequence
<220> FEATURE:
<223> OTHER INFORMATION: Synthetic: Kanmx4-TcycF

<400> SEQUENCE: 25
catttgatgc tcgatgagtt tttctaaatc cgctctaacc gaaaaggaag gag                53

<210> SEQ ID NO 26
<211> LENGTH: 53
<212> TYPE: DNA
<213> ORGANISM: Artificial Sequence
<220> FEATURE:
<223> OTHER INFORMATION: Synthetic: Kanmx4-TcycR

<400> SEQUENCE: 26
ctccttcctt ttcggttaga gcggatttag aaaaactcat cgagcatcaa atg                53

<210> SEQ ID NO 27
<211> LENGTH: 60
<212> TYPE: DNA
<213> ORGANISM: Artificial Sequence
<220> FEATURE:
<223> OTHER INFORMATION: Synthetic: Tcyc-LoxP-NheIR

<400> SEQUENCE: 27
ggggctagca taacttcgta taatgtatgc tatacgaagt tatcttcgag cgtcccaaaa        60

<210> SEQ ID NO 28
<211> LENGTH: 30
<212> TYPE: DNA
<213> ORGANISM: Artificial Sequence
<220> FEATURE:
<223> OTHER INFORMATION: Synthetic: Gpd-BamHIF

<400> SEQUENCE: 28
cgggatccag tttatcatta tcaatactcg                30

<210> SEQ ID NO 29
<211> LENGTH: 31
<212> TYPE: DNA
<213> ORGANISM: Artificial Sequence
<220> FEATURE:
<223> OTHER INFORMATION: Synthetic: Tadh-XhoIR

<400> SEQUENCE: 29
gggctcgagg agcgacctca tgctatacct g                31

<210> SEQ ID NO 30
<211> LENGTH: 22
<212> TYPE: DNA
<213> ORGANISM: Artificial Sequence
<220> FEATURE:
<223> OTHER INFORMATION: Synthetic: Kanmx4R

<400> SEQUENCE: 30
ttagaaaaac tcatcgagca tc                22

<210> SEQ ID NO 31
<211> LENGTH: 55

<212> TYPE: DNA
<213> ORGANISM: Artificial Sequence
<220> FEATURE:
<223> OTHER INFORMATION: Synthetic: OLS 5' FWD

<400> SEQUENCE: 31
gcatagcaat ctaatctaag tttaaaatga atcatttgag agcagaaggg cctgc            55

<210> SEQ ID NO 32
<211> LENGTH: 56
<212> TYPE: DNA
<213> ORGANISM: Artificial Sequence
<220> FEATURE:
<223> OTHER INFORMATION: Synthetic: CB 5' FWD

<400> SEQUENCE: 32
caccagaact tagtttcgac ggataaaatg gaaaccggtt tgtcctcggt ttgcac          56

<210> SEQ ID NO 33
<211> LENGTH: 58
<212> TYPE: DNA
<213> ORGANISM: Artificial Sequence
<220> FEATURE:
<223> OTHER INFORMATION: Synthetic: All REV

<400> SEQUENCE: 33
cataactaat tacatgattt aaccttaaac atcagattca atagagccgc ctccactg       58

<210> SEQ ID NO 34
<211> LENGTH: 8873
<212> TYPE: DNA
<213> ORGANISM: Artificial Sequence
<220> FEATURE:
<223> OTHER INFORMATION: Synthetic

<400> SEQUENCE: 34
ggttaaatca tgtaattagt tatgtcacgc ttacattcac gccctccccc cacatccgct     60
ctaaccgaaa aggaaggagt tagacaacct gaagtctagg tccctattta ttttttttata  120 gttatgttag tattaagaac gttatttata tttcaaattt ttcttttttt tctgtacaga   180
cgcgtgtacg catgtaacat tatactgaaa accttgcttg agaaggtttt gggacgctcg   240
aaggctttaa tttgcggccc ctcacctgca cgcaaaatag gataattata ctctatttct   300
caacaagtaa ttggttgttt ggccgagcgg tctaaggcgc ctgattcaag aaatatcttg   360
accgcagtta actgtgggaa tactcaggta tcgtaagatg caagagttcg aatctcttag   420
caaccattat ttttttcctc aacataacga gaacacacag gggcgctatc gcacagaatc   480
aaattcgatg actggaaatt ttttgttaat ttcagaggtc gcctgacgca tataccttt    540 tcaactgaaa aattgggaga aaaggaaag gtgagagcgc cggaaccggc ttttcatata    600
gaatagagaa gcgttcatga ctaaatgctt gcatcacaat acttgaagtt gacaatatta   660
tttaaggacc tattgttttt tccaataggt ggttagcaat cgtcttactt tctaactttt   720
cttacctttt acatttcagc aatatatata tatatatttc aaggatatac cattctaatg   780
tctgccccta agaagatcgt cgttttgcca ggtgaccacg ttggtcaaga atcacagcc   840 gaagccatta aggttcttaa agctatttct gatgttcgtt ccaatgtcaa gttcgatttc   900
gaaaatcatt taattggtgg tgctgctatc gatgctacag gtgttccact tccagatgag   960
gcgctggaag cctccaagaa ggctgatgcc gttttgttag gtgctgtggg tggtcctaaa  1020
tggggtaccg gtagtgttag acctgaacaa ggtttactaa aaatccgtaa agaacttcaa  1080

```
ttgtacgcca acttaagacc atgtaacttt gcatccgact ctcttttaga cttatctcca   1140
atcaagccac aatttgctaa aggtactgac ttcgttgttg tcagagaatt agtgggaggt   1200
atttactttg gtaagagaaa ggaagatgat ggtgatggtg tcgcttggga tagtgaacaa   1260
tacaccgttc cagaagtgca agaatcaca agaatggccg ctttcatggc cctacaacat    1320
gagccaccat tgcctatttg gtccttggat aaagctaatg ttttggcctc ttcaagatta   1380
tggagaaaaa ctgtggagga aaccatcaag aacgaattcc ctacattgaa ggttcaacat   1440
caattgattg attctgccgc catgatccta gttaagaacc caacccacct aaatggtatt   1500
ataatcacca gcaacatgtt tggtgatatc atctccgatg aagcctccgt tatcccaggt   1560
tccttgggtt tgttgccatc tgcgtccttg gcctctttgc cagacaagaa caccgcattt   1620
ggtttgtacg aaccatgcca cggttctgct ccagatttgc caagaataa ggtcaaccct    1680
atcgccacta tcttgtctgc tgcaatgatg ttgaaattgt cattgaactt gcctgaagaa   1740
ggtaaggcca ttgaagatgc agttaaaaag gttttggatg caggcatcag aactggtgat   1800
ttaggtggtt ccaacagtac caccgaagtc ggtgatgctg tcgccgaaga agttaagaaa   1860
atccttgctt aaaaagattc tcttttttta tgatatttgt acataaactt tataaatgaa   1920
attcataata gaaacgacac gaaattacaa aatggaatat gttcataggg taacgctatg   1980
atccaatatc aaaggaaatg atagcattga aggatgagac taatccaatt gaggagtggc   2040
agcatataga acagctaaag ggtagtgctg aaggaagcat acgatacccc gcatggaatg   2100
ggataatatc acaggaggta ctagactacc tttcatccta cataaataga cgcatataag   2160
tacgcattta agcataaaca cgcactatgc cgttcttctc atgtatatat atatacaggc   2220
aacacgcaga tataggtgcg acgtgaacag tgagctgtat gtgcgcagct cgcgttgcat   2280
tttcggaagc gctcgttttc ggaaacgctt gaagttcct attccgaagt tcctattctc    2340
tagaaagtat aggaacttca gagcgctttt gaaaaccaaa agcgctctga gtcgcactt    2400
tcaaaaaacc aaaaacgcac cggactgtaa cgagctacta aaatattgcg aataccgctt   2460
ccacaaacat tgctcaaaag tatctctttg ctatatatct ctgtgctata ccctatata    2520
acctacccat ccaccttcg ctccttgaac ttgcatctaa actcgacctc tacattttt    2580
atgtttatct ctagtattac tctttagaca aaaaaattgt agtaagaact attcatagag   2640
tgaatcgaaa acaatacgaa aatgtaaaca tttcctatac gtagtatata gagacaaaat   2700
agaagaaacc gttcataatt ttctgaccaa tgaagaatca tcaacgctat cactttctgt   2760
tcacaaagta tgcgcaatcc acatcggtat agaatataat cggggatgcc tttatcttga   2820
aaaaatgcac ccgcagcttc gctagtaatc agtaaacgcg ggaagtggag tcaggctttt   2880
tttatggaag agaaaataga caccaaagta gccttcttct aaccttaacg gacctacagt   2940
gcaaaaagtt atcaagagac tgcattatag agcgcacaaa ggagaaaaaa agtaatctaa   3000
gatgctttgt tagaaaaata gcgctctcgg gatgcatttt tgtagaacaa aaaagaagta   3060
tagattcttt gttggtaaaa tagcgctctc gcgttgcatt tctgttctgt aaaaatgcag   3120
ctcagattct tgtttgaaa aattagcgct ctcgcgttgc attttgttt tacaaaaatg    3180
aagcacagat tcttcgttgg taaaatagcg ctttcgcgtt gcatttctgt tctgtaaaaa   3240
tgcagctcag attctttgtt tgaaaaatta gcgctctcgc gttgcatttt tgttctacaa   3300
aatgaagcac agatgcttcg ttcaggtggc acttttcggg gaaatgtgcg cggaacccct   3360
atttgtttat ttttctaaat acattcaaat atgtatccgc tcatgagaca ataaccctga   3420
tattggtcag aattggttaa ttggttgtaa cactgacccc tatttgttta ttttttctaaa  3480
```

```
tacattcaaa tatgtatccg ctcatgagac aataaccctg ataaatgctt caataatatt   3540
gaaaaaggaa gaatatgagc catattcaac gggaaacgtc gaggccgcga ttaaattcca   3600
acatggatgc tgatttatat gggtataaat gggctcgcga taatgtcggg caatcaggtg   3660
cgacaatcta tcgcttgtat gggaagcccg atgcgccaga gttgtttctg aaacatggca   3720
aaggtagcgt tgccaatgat gttacagatg agatggtcag actaaactgg ctgacggaat   3780
ttatgccact tccgaccatc aagcatttta tccgtactcc tgatgatgca tggttactca   3840
ccactgcgat ccccggaaaa acagcgttcc aggtattaga agaatatcct gattcaggtg   3900
aaaatattgt tgatgcgctg gcagtgttcc tgcgccggtt gcactcgatt cctgtttgta   3960
attgtccttt taacagcgat cgcgtatttc gcctcgctca ggcgcaatca cgaatgaata   4020
acggtttggt tgatgcgagt gattttgatg acgagcgtaa tggctggcct gttgaacaag   4080
tctggaaaga aatgcataaa cttttgccat tctcaccgga ttcagtcgtc actcatggtg   4140
atttctcact tgataacctt atttttgacg aggggaaatt aataggttgt attgatgttg   4200
gacgagtcgg aatcgcagac cgataccagg atcttgccat cctatggaac tgcctcggtg   4260
agttttctcc ttcattacag aaacggcttt tcaaaaata tggtattgat aatcctgata   4320
tgaataaatt gcaatttcat ttgatgctcg atgagttttt ctaactcatg accaaaatcc   4380
cttaacgtga gttacgcgcg cgtcgttcca ctgagcgtca gaccccgtag aaagatcaa   4440 aggatcttct tgagatcctt ttttctgcg cgtaatctgc tgcttgcaaa caaaaaaacc   4500
accgctacca gcggtggttt gtttgccgga tcaagagcta ccaactcttt ttccgaaggt   4560
aactggcttc agcagagcgc agataccaaa tactgttctt ctagtgtagc cgtagttagc   4620
ccaccacttc aagaactctg tagcaccgcc tacatacctc gctctgctaa tcctgttacc   4680
agtggctgct gccagtggcg ataagtcgtg tcttaccggg ttggactcaa gacgatagtt   4740
accggataag gcgcagcggt cgggctgaac ggggggttcg tgcacacagc ccagcttgga   4800
gcgaacgacc tacaccgaac tgagatacct acagcgtgag ctatgagaaa gcgccacgct   4860
tcccgaaggg agaaaggcgg acaggtatcc ggtaagcggc agggtcggaa caggagagcg   4920
cacgagggag cttccagggg gaaacgcctg gtatctttat agtcctgtcg ggtttcgcca   4980
cctctgactt gagcgtcgat ttttgtgatg ctcgtcaggg gggcggagcc tatggaaaaa   5040
cgccagcaac gcggcctttt tacggttcct ggccttttgc tggccttttg ctcacatgtt   5100
ctttcctgcg ttatcccctg attctgtgga taaccgtatt accgcctttg agtgagctga   5160
taccgctcgg ggtcgtgcag gtagtttatc attatcaata ctcgccattt caagaatac   5220 gtaaataatt aatagtagtg attttcctaa ctttatttag tcaaaaaatt agccttttaa   5280
ttctgctgta acccgtacat gcccaaaata ggggggcgggt tacacagaat atataacatc   5340
gtaggtgtct gggtgaacag tttattcctg gcatccacta aatataatgg agcccgcttt   5400
ttaagctggc atccagaaaa aaaaagaatc ccagcaccaa aatattgttt tcttcaccaa   5460
ccatcagttc ataggtccat tctcttagcg caactacaga gaacaggggc acaaacaggc   5520
aaaaaacggg cacaacctca atggagtgat gcaaccagcc tggagtaaat gatgacacaa   5580
ggcaattgac ccacgcatgt atctatctca ttttcttaca ccttctatta ccttctgctc   5640
tctctgattt ggaaaaagct gaaaaaaaag gttgaaacca gttccctgaa attattcccc   5700
tacttgacta ataagtatat aaagacggta ggtattgatt gtaattctgt aaatctatt   5760 cttaaacttc ttaaattcta ctttatagt tagtcttttt tttagttttta aaacaccaga   5820
```

```
acttagtttc gacggataaa atggaaaccg gtttgtcctc ggtttgcact ttctccttcc    5880
aaacaaacta tcatacactc ctgaacccgc acaataacaa tcccaaaact tccctgctgt    5940
gttataggca cccaaagaca ccaatcaaat actcctacaa taactttcca tctaagcatt    6000
gtagcacaaa aagtttccat ttgcaaaata agtgttccga atctctgtcc atcgccaaaa    6060
attccattag ggctgccact actaatcaaa ctgaaccacc agagtctgat aatcattctg    6120
tcgccacaaa gattctgaat tttgggaagg cttgttggaa gttacaaaga ccatatacaa    6180
ttattgcctt tacctcttgt gcctgtggtt tatttggtaa ggaactgttg cataatacaa    6240
atttaatatc ttggtcattg atggaaacgt tcaaagcatt ttttttctta gtcgctatcc    6300
tttgtattgc ttctttcacc accactatca accagattta cgacttacat attgacagaa    6360
ttaacaagcc agatttgcca ctggcttcgg gcgagatttc cgtcaatact gcctggatca    6420
tggaaacttc tattattgtt gccttgtttg gattgataat caccataaaa atggaaacta    6480
agggtggtcc attgtatatt ttcggttact gttttggtat cttcgggggc atcgtctact    6540
ctgttcctcc attcagatgg aaacaaaatc cttccacagc attcctttg aacttcctgg     6600
cgcacattat aaccaacttt acttttatt atgcctccag agccgccctg gggctgccct     6660
ttgaattacg cccctccttt acattttac tggccttcat ggagaccaag tccatggaga      6720
ctggttctgc tctcgcgttg atcaaagatg cttccgatgt ggaaggtgac accaaatttg    6780
gtatatccac tttggccagc aagtatggtt ccaggaattt gaccctattt tgttctggta    6840
tcgtgctgct gtcttatgtt gcagccatct tggctggcat catttggcca caggctttca    6900
attcaaatgt tatggagacg ctgctctcgc atgctatttt ggcattttgg ttgattctac    6960
agacaagaga ttttgcttta accaattatg acccagaagc tggtagaaga ttttacgaat    7020
ttatggaaac atgaaattta actatgctg aatatttagt gtacgttttc attggggggcg     7080
gctccagcgc cggcggcggc tcttctgcgg gcggttggtc tcatccacaa tttgagaaag    7140
gtgggtcgtc tggcggcggc agcgggggcg ggtccggcgg gggagcggc ggtatgaaat      7200
gttcgacctt ctctttttgg tttgtctgta aaataatttt tttttcttc agctttaaca      7260
ttcaaaccag cattgcaaat ccaagagaaa atttcttgaa atgcttttca caatatatcc    7320
ccaataatgc tactaacttg aagctagttt atactcaaaa caacccttg tacatgtccg      7380
tgctcaactc caccattcac aacctaagat tcacttcaga cactacccca aaaccattag    7440
ttattgtgac accttctcac gtttcacata tccaaggtac tattttatgc tccaagaagg    7500
tcggcctgca aattagaact agatctggag gtcatgattc agaaggaatg tcttacatct    7560
ctcaagttcc atttgtgatt gtcgatttaa gaaatatgag gagcattaag atcgatgttc    7620
actcccaaac ggcatgggtt gaagccggtg ccaccttggg cgaagtttac tactgggtca    7680
acgagaagaa tgaaaactta tcactagccg caggttattg tccaactgtt tgtgctggtg    7740
gccatttcgg aggcggcggc tacggtcctc taatgagaaa ctacggctta gctgctgaca    7800
atatcatcga cgctcacttg gttaacgttc atggtaaagt tttagataga aaatctatgg    7860
gtgaggatct tttctgggct ttgagaggtg gcggcgcaga atcatttggc attatcgttg    7920
cttggaagat cagattggtg gctgtcccca agtctacaat gttttctgtg aagaaaatta    7980
tggaaatcca tgaattggtc aaactggtga ataaatggca aaacatagct tacaagtacg    8040
ataaagactt gctgttaatg acacatttta ttaccaggaa catcactgat aaccaaggca    8100
agaacaagac tgcaattcat acttattttt cctccgtttt tttgggtggt gtcgactccc    8160
tcgtggatct gatgaataaa tcattccctg aactaggtat taaaaaaacc gattgtagac    8220
```

```
aattgagttg gattgatacc atcatattct acagtggtgt tgttaattat gatactgaca      8280
acttcaacaa agaaatactg ctggaccgtt ccgccggcca gaatggtgct tttaaaatca      8340
agttggatta tgtgaaaaag cctattccag aatccgtatt tgttcaaata ttggaaaagc      8400
tgtatgaaga agacattggt gcaggcatgt acgctcttta tccttatggc ggcataatgg      8460
atgaaatttc tgaaagtgcc attcctttcc cacatagggc cgggatcctg tacgagttat      8520
ggtacatttg ttcatgggaa aagcaagaag ataatgaaaa acatttaaat tggataagaa      8580
atatttataa ttttatgact ccatacgtct ccaaaaaccc acgcctggca tatttgaatt      8640
acagagacct ggatattggc atcaatgatc ctaaaaaccc aaataattac actcaggcaa      8700
gaatatgggg tgaaaaatat ttcggcaaaa attttgatag gctggtcaag gttaaaacac      8760
tggttgatcc aaacaatttc tttagaaacg aacaatctat cccacctctg cctagacata      8820
gacacggcgg tggaagcagt ggaggcggct ctattgaatc tgatgtttaa tga           8873
```

<210> SEQ ID NO 35
<211> LENGTH: 6677
<212> TYPE: DNA
<213> ORGANISM: Artificial Sequence
<220> FEATURE:
<223> OTHER INFORMATION: Synthetic

<400> SEQUENCE: 35

```
ggttaaatca tgtaattagt tatgtcacgc ttacattcac gccctccccc cacatccgct        60
ctaaccgaaa aggaaggagt tagacaacct gaagtctagg tccctattta tttttttata       120
gttatgttag tattaagaac gttatttata tttcaaattt ttcttttttt tctgtacaga       180
cgcgtgtacg catgtaacat tatactgaaa accttgcttg agaaggtttt gggacgctcg       240
aaggctttaa tttgcggccc ctcacctgca cgcaaaaagc ttttcaattc aattcatcat       300 tttttttta ttctttttt tgatttcggt ttctttgaaa ttttttttgat tcggtaatct       360 ccgaacagaa ggaagaacga aggaaggagc acagacttag attggtatat atacgcatat       420
gtagtgttga agaaacatga aattgcccag tattcttaac ccaactgcac agaacaaaaa       480
ccagcaggaa acgaagataa atcatgtcga aagctacata taaggaacgt gctgctactc       540
atcctagtcc tgttgctgcc aagctatta atatcatgca cgaaaagcaa acaaacttgt       600
gtgcttcatt ggatgttcgt accaccaagg aattactgga gttagttgaa gcattaggtc       660
ccaaaatttg tttactaaaa acacatgtgg atatcttgac tgattttcc atggagggca       720 cagttaagcc gctaaaggca ttatccgcca agtacaattt tttactcttc gaagatagaa       780
aatttgctga cattggtaat acagtcaaat gcagtactc tgcgggtgta tacagaatag       840
cagaatgggc agacattacg aatgcacacg gtgtggtggg cccaggtatt gttagcggtt       900
tgaagcaggc ggcagaagaa gtaacaaagg aacctagagg cctttttgatg ttagcagaat       960 tgtcatgcaa gggctcccta tctactggag aatatactaa gggtactgtt gacattgcga      1020
aaagcgacaa agattttgtt atcggcttta ttgctcaaag agacatgggt ggaagagatg      1080
aaggttacga ttggttgatt atgacacccg gtgtgggttt agatgacaag ggagatgcat      1140
tgggtcaaca gtatagaacc gtggatgatg ttgtctctac aggatctgac attattattg      1200
ttggaagagg actatttgca aagggaaggg atgctaaggt agagggtgaa cgttacagaa      1260
aagcaggctg ggaagcatat ttgagaagat gcggccagca aaaactaaaaa actgtattat      1320 aagtaaatgc atgtatacta aactcacaaa ttagagcttc aatttaatta tatcagttat      1380
```

```
tacccacgct atgatccaat atcaaaggaa atgatagcat tgaaggatga gactaatcca    1440
attgaggagt ggcagcatat agaacagcta aagggtagtg ctgaaggaag catacgatac    1500
cccgcatgga atgggataat atcacaggag gtactagact acctttcatc ctacataaat    1560
agacgcatat aagtacgcat ttaagcataa acacgcacta tgccgttctt ctcatgtata    1620
tatatataca ggcaacacgc agatataggt gcgacgtgaa cagtgagctg tatgtgcgca    1680
gctcgcgttg cattttcgga agcgctcgtt ttcggaaacg cttttgaagtt cctattccga    1740 agttcctatt ctctagaaag tataggaact tcagagcgct tttgaaaacc aaaagcgctc    1800
tgaagtcgca ctttcaaaaa accaaaaacg caccggactg taacgagcta ctaaaatatt    1860
gcgaataccg cttccacaaa cattgctcaa aagtatctct ttgctatata tctctgtgct    1920
atatccctat ataacctacc catccacctt tcgctccttg aacttgcatc taaactcgac    1980
ctctacattt tttatgttta tctctagtat tactctttag acaaaaaaat tgtagtaaga    2040
actattcata gagtgaatcg aaaacaatac gaaaatgtaa acatttccta tacgtagtat    2100
atagagacaa aatagaagaa accgttcata atttttctgac caatgaagaa tcatcaacgc    2160
tatcactttc tgttcacaaa gtatgcgcaa tccacatcgg tatagaatat aatcggggat    2220
gcctttatct tgaaaaaatg cacccgcagc ttcgctagta atcagtaaac gcgggaagtg    2280
gagtcaggct ttttttatgg aagagaaaat agacaccaaa gtagccttct tctaacctta    2340
acggacctac agtgcaaaaa gttatcaaga gactgcatta tagagcgcac aaaggagaaa    2400
aaaagtaatc taagatgctt tgttagaaaa atagcgctct cgggatgcat ttttgtagaa    2460 caaaaagaa gtatagattc tttgttggta aaatagcgct ctcgcgttgc atttctgttc    2520
tgtaaaaatg cagctcagat tctttgtttg aaaaattagc gctctcgcgt tgcattttttg    2580 ttttacaaaa atgaagcaca gattcttcgt tggtaaaata gcgctttcgc gttgcatttc    2640
tgttctgtaa aaatgcagct cagattcttt gtttgaaaaa ttagcgctct cgcgttgcat    2700
ttttgttcta caaatgaag cacagatgct tcgttcaggt ggcacttttc ggggaaatgt    2760
gcgcggaacc cctatttgtt tatttttcta aatacattca aatatgtatc cgctcatgag    2820
acaataaccc tgatattggt cagaattggt taattggttg taacactgac ccctatttgt    2880
ttatttttct aaatacattc aaatatgtat ccgctcatga acaataaccc tgataaatg    2940 cttcaataat attgaaaaag gaagaatatg agtattcaac atttccgtgt cgcccttatt    3000 ccctttttg cggcattttg ccttcctgtt tttgctcacc cagaaacgct ggtgaaagta    3060
aaagatgctg aagatcagtt gggtgcacga gtgggttaca tcgaactgga tctcaacagc    3120
ggtaagatcc ttgagagttt tcgccccgaa gaacgttttc caatgatgag cacttttaaa    3180
gttctgctat gtggcgcggt attatcccgt attgacgccg ggcaagagca actcggtcgc    3240
cgcatacact attctcagaa tgacttggtt gagtactcac cagtcacaga aaagcatctt    3300
acggatggca tgacagtaag agaattatgc agtgctgcca taaccatgag tgataacact    3360
gcggccaact tacttctgac aacgatcgga ggaccgaagg agctaaccgc ttttttgcac    3420
aacatggggg atcatgtaac tcgccttgat cgttgggaac cggagctgaa tgaagccata    3480
ccaaacgacg agcgtgacac cacgatgcct gtagcgatgg caacaacgtt gcgcaaacta    3540
ttaactggcg aactacttac tctagcttcc cggcaacaat taatagactg gatggaggcg    3600
gataaagttg caggaccact tctgcgctcg gcccttccgg ctggctggtt tattgctgat    3660
aaatccggag ccggtgagcg tggttctcgc ggtatcatcg cagcgctggg gccagatggt    3720
aagccctccc gtatcgtagt tatctacacg acggggagtc aggcaactat ggatgaacga    3780
```

```
aatagacaga tcgctgagat aggtgcctca ctgattaagc attggtaact catgaccaaa   3840
atcccttaac gtgagttacg cgcgcgtcgt tccactgagc gtcagacccc gtagaaaaga   3900
tcaaaggatc ttcttgagat cctttttttc tgcgcgtaat ctgctgcttg caaacaaaaa   3960
aaccaccgct accagcggtg gtttgtttgc cggatcaaga gctaccaact cttttttccga  4020 aggtaactgg cttcagcaga gcgcagatac caaatactgt tcttctagtg tagccgtagt   4080
tagcccacca cttcaagaac tctgtagcac cgcctacata cctcgctctg ctaatcctgt   4140
taccagtggc tgctgccagt ggcgataagt cgtgtcttac cgggttggac tcaagacgat   4200
agttaccgga taaggcgcag cggtcgggct gaacggggggg ttcgtgcaca cagcccagct  4260
tggagcgaac gacctacacc gaactgagat acctacagcg tgagctatga gaaagcgcca   4320
cgcttcccga aggagaaag gcggacaggt atccggtaag cggcagggtc ggaacaggag    4380
agcgcacgag ggagcttcca gggggaaacg cctggtatct ttatagtcct gtcgggtttc   4440
gccacctctg acttgagcgt cgatttttgt gatgctcgtc aggggggcgg agcctatgga   4500
aaaacgccag caacgcggcc ttttacggt tcctggcctt tgctggcct tttgctcaca     4560 tgttctttcc tgcgttatcc cctgattctg tggataaccg tattaccgcc tttgagtgag   4620
ctgataccgc tcgggtcgt gcaggtatag cttcaaaatg tttctactcc ttttttactc    4680
ttccagattt tctcggactc cgcgcatcgc cgtaccactt caaaacaccc aagcacagca   4740
tactaaattt cccctctttc ttcctctagg gtgtcgttaa ttacccgtac taaaggtttg   4800
gaaaagaaaa aagtgaccgc ctcgtttctt tttcttcgtc gaaaaaggca ataaaaattt   4860
ttatcacgtt tcttttttctt gaaaattttt ttttttgatt ttttttctctt tcgatgacct  4920 cccattgata tttaagttaa taaacggact tcaatttctc aagtttcagt ttcattttttc  4980 ttgttctatt acaactttttt ttacttcttg ctcattagaa agaaagcata gcaatctaat  5040
ctaagtttaa aatgaatcat ttgagagcag aagggcctgc ttccgtgctg gctattggta   5100
ccgccaatcc agaaaatatc ctgctgcagg acgaattccc agattactat tttagggtca   5160
ccaaatctga acatatgaca caattgaaag agaaattcag aaagatttgt gacaagtcca   5220
tgattaggaa aagaaattgt ttttttgaatg aagaacactt gaagcaaaat cctcgcctgg   5280
tggagcatga aatgcaaact ttggatgcta gacaagacat gttggtggtg gaagttccaa   5340
agctggggaa ggatgcctgt gccaaggcca ttaagaatg gggccaacca aaatccaaaa    5400
ttacccacct gattttcacc tccgcctcca ccactgatat gccaggtgca gactatcatt   5460
gtgctaaatt gttgggtttg tccccctccg tgaagagagt tatgatgtat caattaggtt   5520
gttatggcgg cggcaccgtt ctgagaattg ccaaagacat tgctgaaaac aataaggtg    5580 cgcgcgtttt ggctgtttgt tgtgatatta tggcatgttt atttagaggt ccaagtgaaa   5640
gtgacttgga attgctagtg ggccaggcca tatttggtga tggtgccgct gctgtgatcg   5700
ttggtgctga gcctgatgaa tctgtcggtg aaagaccaat ttttgaactg gtttccactg   5760
gtcaaaccat tttgccaaat tcagaaggta ctattggcgg ccatatcaga gaagctggtt   5820
taatctttga tttgcacaag gatgtcccaa tgttaatttc caataatatt gaaaaatgtt   5880
tgatcgaagc atttacccccc atcggtattt ctgattggaa ttccatcttc tggattacac   5940
atcctggcgg taaagctatc ttagataaag ttgaggagaa gttgcattta aagtctgaca   6000
aatttgttga ttcaagacat gtcctgtctg agcacggtaa tatgtcttcc tcgaccgtct   6060
tgtttgtcat ggatgagttg aggaagaggt ccctggaaga aggcaagagc accaccggtg   6120
```

| | |
|---|---|
| acggttttga gtgggggtc ctctttggat ttgggccagg cctgaccgta gaaagggttg | 6180 |
| ttgtccgctc ggtgccaatc aaatatggtg ggggtccag cgccggtggc gggagctccg | 6240 |
| cgggcggttg gtctcaccca caatttgaaa agggtggcag cagcggcggc ggctctggcg | 6300 |
| gaggctccgg cggggctcg gggggtatgg ctgtcaagca tctgatcgtg ctgaagttca | 6360 |
| aagatgaaat tactgaagcc caaaaggagg aattttttcaa gacatatgtt aatttggtta | 6420 |
| acatcattcc agcaatgaaa gatgtttatt ggggtaagga cgttactcaa aaaaataagg | 6480 |
| aagagggtta cactcatatt gttgaagtca ctttcgaatc cgtcgaaaca attcaagatt | 6540 |
| atattattca tccagctcat gttgggtttg gcgatgtgta cagatcattt tgggaaaaat | 6600 |
| tattgatttt tgactacaca ccaagaaaag gcggtggaag cagtggaggc ggctctattg | 6660 |
| aatctgatgt ttaatag | 6677 |

<210> SEQ ID NO 36
<211> LENGTH: 3372
<212> TYPE: DNA
<213> ORGANISM: Artificial Sequence
<220> FEATURE:
<223> OTHER INFORMATION: Synthetic

<400> SEQUENCE: 36

| | |
|---|---|
| atggagaaga ctcaagaaac agtccaaaga attcttctag aaccctataa atacttactt | 60 |
| cagttaccag gtaaacaagt gagaaccaaa ctttcacagg catttaatca ttggctgaaa | 120 |
| gttccagagg acaagctaca gattattatt gaagtgacag aaatgttgca taatgccagt | 180 |
| ttactcatcg atgatattga agacaactca aaactccgac gtggctttcc agtggcccac | 240 |
| agcatctatg gaatcccatc tgtcatcaat tctgccaatt acgtgtattt ccttggcttg | 300 |
| gagaaagtct taacccttga tcacccagat gcagtgaagc tttttacccg ccagcttttg | 360 |
| gaactccatc agggacaagg cctagatatt tactggaggg ataattacac ttgtcccact | 420 |
| gaagaagaat ataaagctat ggtgctgcag aaaacaggtg gactgtttgg attagcagta | 480 |
| ggtctcatgc agttgttctc tgattacaaa gaagatttaa aaccgctact aatacactt | 540 |
| gggctctttt tccaaattag ggatgattat gctaatctac actccaaaga atatagtgaa | 600 |
| aacaaaagtt tttgtgaaga tctgacagag ggaaagttct catttcctac tattcatgct | 660 |
| atttggtcaa ggcctgaaag cacccaggtg cagaatatct gcgccagag aacagaaaac | 720 |
| atagatataa aaaaatactg tgtacattat cttgaggatg taggttcttt tgaatacact | 780 |
| cgtaataccc ttaaagagct tgaagctaaa gcctataaac agattgatgc acgtggtggg | 840 |
| aaccctgagc tagtagcctt agtaaaacac ttaagtaaga tgttcaaaga agaaatgaa | 900 |
| ggcggttctg gcagcggaga gggcagagga agtcttctaa catgcggtga cgtggaggag | 960 |
| aatcccggcc ctaggtctgg cagcggagag ggcagaggaa gtcttctaac atgcggtgac | 1020 |
| gtggaggaga tcccggccc taggacacaa aagaaagtcc cagacaattg ttgtagacgt | 1080 |
| gaacctatgc tggtcagaaa taccagaaaa tgtgattcag tagaggaaga gacagggata | 1140 |
| aaccgagaaa gaaagttga ggttataaaa cccttagtgg ctgaaacaga taccccaaac | 1200 |
| agagctacat ttgtgttgg taactcctcc ttactcgata cttcatcagt actggtgaca | 1260 |
| caggaacctg aaattgaact tcccagggaa cctcggccta atgaagaatg tctacagata | 1320 |
| cttgggaatg cagagaaagg tgcaaaattc cttagtgatg ctgagatcat ccagttagtc | 1380 |
| aatgctaagc atatcccagc ctacaagttg gaaactctga tggaaactca tgagcgtggt | 1440 |
| gtatctattc gccgacagtt actttccaag aagctttcag aaccttcttc tctccagtac | 1500 |

-continued

```
ctaccttaca gggattataa ttactccttg gtgatgggag cttgttgtga gaatgttatt    1560
ggatatatgc ccatccctgt tggagtggca ggaccccttt gcttagatga aaaagaattt    1620
caggttccaa tggcaacaac agaaggttgt cttgtggcca gcaccaatag aggctgcaga    1680
gcaataggtc ttggtggagg tgccagcagc cgagtccttg cagatgggat gactcgtggc    1740
ccagttgtgc gtcttccacg tgcttgtgac tctgcagaag tgaaagcctg gctcgaaaca    1800
tctgaagggt tcgcagtgat aaaggaggca tttgacagca ctagcagatt tgcacgtcta    1860
cagaaacttc atacaagtat agctggacgc aacctttata tccgtttcca gtccaggtca    1920
ggggatgcca tggggatgaa catgatttca aagggtacag agaaagcact ttcaaaactt    1980
cacgagtatt tccctgaaat gcagattcta gccgttagtg gtaactattg tactgacaag    2040
aaacctgctg ctataaattg gatagaggga agaggaaaat ctgttgtttg tgaagctgtc    2100
attccagcca aggttgtcag agaagtatta aagactacca cagaggctat gattgaggtc    2160
aacattaaca agaatttagt gggctctgcc atggctggga gcataggagg ctacaacgcc    2220
catgcagcaa acattgtcac cgccatctac attgcctgtg gacaggatgc agcacagaat    2280
gttggtagtt caaactgtat tactttaatg gaagcaagtg gtcccacaaa tgaagattta    2340
tatatcagct gcaccatgcc atctatagag ataggaacgg tgggtggtgg gaccaaccta    2400
ctacctcagc aagcctgttt gcagatgcta ggtgttcaag gagcatgcaa agataatcct    2460
ggggaaaatg cccggcagct tgcccgaatt gtgtgtggga ccgtaatggc tggggaattg    2520
tcacttatgg cagcattggc agcaggacat cttgtcaaaa gtcacatgat tcacaacagg    2580
tcgaagatca atttacaaga cctccaagga gcttgcacca agaagacagc cggctcagga    2640
ggttcttcag gactggaagt gctgtttcag ggcccgggtg gatctggcat gatgcctgaa    2700
ataaacacta accacctcga caagcaacag gttcaactcc tggcagagat gtgtatcctt    2760
attgatgaaa atgacaataa aattggagct gagaccaaga agaattgtca cctgaacgag    2820
aacattgaga aaggattatt gcatcgagct tttagtgtct tcttattcaa caccgaaaat    2880
aagcttctgc tacagcaaag atcagatgct aagattacct ttccaggttg ttttacgaat    2940
acgtgttgta gtcatccatt aagcaatcca gccgagcttg aggaaagtga cgcccttgga    3000
gtgaggcgag cagcacagag acggctgaaa gctgagctag gaattccctt ggaagaggtt    3060
cctccagaag aaattaatta tttaacacga attcactaca aagctcagtc tgatggtatc    3120
tggggtgaac atgaaattga ttacattttg ttggtgagga agaatgtaac tttgaatcca    3180
gatcccaatg agattaaaag ctattgttat gtgtcaaagg aagaactaaa agaacttctg    3240
aaaaaagcag ccagtggtga aattaagata acgccatggt ttaaaattat tgcagcgact    3300
tttctctttta aatggtggga taacttaaat catttgaatc agtttgttga ccatgagaaa    3360
atatacagaa tg                                                        3372
```

ISOLATED CODON OPTIMIZED NUCLEIC ACID

RELATED APPLICATIONS

The present application is a continuation of U.S. Ser. No. 15/096,164, filed Apr. 11, 2016, entitled "A Novel Method for the Cheap, Efficient, and Effective Production of Pharmaceutical and Therapeutic API's, Intermediate, and Final Products", that claims the benefit of U.S. Provisional Patent Application Ser. No. 62/145,430, entitled "A Novel Method for the Cheap, Efficient, and Effective Production of Pharmaceutical and Therapeutic API's, Intermediate, and Final Products", filed Apr. 9, 2015, both of which are herein incorporated by reference in their entirety for all purposes.

REFERENCE TO AN ELECTRONIC SEQUENCE LISTING

The contents of the electronic Sequence Listing submitted in ASCII format via EFS-WEB (created on Dec. 12, 2017; named CBT_USCON. ST25.txt; 30.808 bytes in size) is herein incorporated by reference in its entirety.

FIELD OF THE INVENTION

The present invention is in the technical field of large scale production of pharmaceutical and supplemental products for various common illnesses, medical conditions, and general industrial use. More particularly, the present invention is in the technical field of bio-synthesis of cannabinoids, terpenoids, stilbenoids, flavonoids, phenolic amides, lignanamides, spermidine alkaloids, and phenylpropanoids; compounds found in *Cannabis sativa*, along with various combinations and specialized formulations which are beneficial in ailments ranging from cancer to glaucoma. The final product(s) can be an intermediate or a compound of interest. The core concept of the invention is based on the idea of cheaper and more efficient production, along with novel products and applications.

BACKGROUND OF THE INVENTION

Cannabinoids from *Cannabis* have been used for thousands of years for treatment of various ailments and conditions in many different cultures around the world. However, most of various types of cannabinoids in *Cannabis* are at a very low concentration in the plant. Therefore, most patients/users never get a threshold dosage for any kind of relief from anything other than tetrahydrocannabinolic acid (THC/A), cannabinolic-acid (CBD/A), and cannabinol (CBN). There are a few strains or concentrates available that have a rare cannabinoid, but are usually very highly concentrated in tetrahydrocannabinol (THC) or cannabidiol (CBD) to have any pronounced effect by the rare cannabinoid.

In other words, the pharmaceutical industry has not tapped into the real potential of the *Cannabis* plant. With time, more research is being conducted into the different kinds of cannabinoids and their medicinal applications. Researchers are finding that many of the other cannabinoids also have unique medicinal properties.

SUMMARY OF THE INVENTION

Biosynthesis of important molecules can be used for therapeutic applications, bulk substance production, intermediate API biosynthesis, and various other novel formulations and applications for such substances, as known to those skilled in the art. Many biological molecules can be changed/converted into molecules of importance by using enzymes and other processes. This process can be utilized by employing methods for transforming a range of starting materials into final products to be used in pharmaceuticals and supplements as active ingredients, or donating a significant portion of their structure to the final active ingredients. The final products can also be used in other industries and applications, such as food, beverage, and other goods production. For example, table sugar, starch, and cellulose can be converted to glucose, creating a molecule that can readily be utilized by any organism as an energy source. Therefore, depending on the specific compound(s) being manufactured, and the kind(s) of starting materials available, along with the host and production technique(s) any kind of host engineering, various expression systems and methods, and varying materials, a spectrum of different methods and products is possible.

The advantages of the present invention include, without limitation, creation of hundreds of compounds from readily available biological molecules that can be produced and harvested from virtually all known sources of plants and other energy producing organisms. Since sugar producing plants and organisms, biomass, and carbon based industrial waste products are very abundant, our "raw material" will be very cheap and easy to obtain anywhere in the world. After scaling up the given methods, hundreds of compounds with medicinal properties can be produced at a very low cost, allowing the widespread distribution and aiding of millions of people.

Another advantage is that there is no need or use of growing any illegal plants. For example, no marijuana, poppy, or other plant production is necessary. This is advantageous as it will lead to drastically cutting down the production, consumption, and trafficking of many unregulated substances.

The most important advantage of the present invention is that we can make and use many compounds that are virtually so low in concentration in the *Cannabis* plant, that there is no effect in using *Cannabis* if we are only after the therapeutic effects of these compounds. For example, patients using marijuana can only benefit from tetrahydrocannabinolic acic (THCA), THC, cannabidiolic acid (CBDA), CBD, CBN, and a few other compound class families, as the concentrations of the other compounds is so low that it has no effect. This invention will allow the production of hundreds of compounds in pure form, leading to many new medical discoveries and applications.

BRIEF DESCRIPTION OF THE FIGURES

The nature, objects, and advantages of the present invention will become more apparent to those skilled in the art after considering the following detailed description in connection with the accompanying figures, in which like reference numerals designate like parts throughout, and wherein:

FIG. 1 is a diagram of the pathway for the biosynthesis of all molecules of interest via the conversion of starting materials to glucose and then to final products;

FIG. 2 is a diagram of the pathway for the biosynthesis of cannabinoids;

FIG. 3 is a diagram of the pathway for the biosynthesis of stilbenoids;

FIG. 4 is a diagram of the pathway for the biosynthesis of phenylpropanoids and flavonoids;

FIG. 5 is a diagram of the pathway for the biosynthesis of phenolic amides and ligananamides;

FIG. 6 is a diagram of the pathway for the biosynthesis of spermidine alkaloids;

FIG. 7 is a diagram of the combined biosynthetic pathways of FIGS. 1-6; and FIG. 8 is diagram of the genetic modification of certain genes for higher product yield in *Saccharomyces cerevisiae* yeast.

DETAILED DESCRIPTION OF THE INVENTION

The present invention is a method for the biosynthesis of hundreds of compounds, mainly found in the *Cannabis* plant. The starting material for these compounds can be any biological compound that is used/produced in a biological organism from the sugar family starting materials or other low cost raw materials processed via enzymes or within organisms to give final products. These final products include, but are not limited to: cannabinoids, terpenoids, stilbenoids, flavonoids, phenolic amides, lignanamides, spermidine alkaloids, and phenylpropanoids (collectively, "final products").

Definitions, Terms, Elements

The Following are a List of Terms and their Definitions:
Genetic engineering: targeted manipulation of a cell's genetic information
Rational Metabolic Engineering: engineering of enzymes, transporters, or regulatory proteins based on available information about enzymes, pathways, and their regulation.
Evolutionary engineering: encompasses all methods for empirical strain improvement (mutagenesis [natural or induced] and recombination and/or shuffling of genes, pathways, and even whole cells; usually performed in cycles or sequentially
Cannabinoids: compounds that are terpenophenolic with 22 carbons (21 carbons for neutral forms), found in *Cannabis*
Terpenoids: also known as isoprenoids, class of organic compounds
Stilbenoids: hydroxylated derivatives of stilbene
Flavonoids/phenylpropanoids: compounds derived from or using phenylalanine as a precursor
Lignanamides/phenolic amides: compounds produced through tyramine pathways
Spermidine alkaloids: compounds produced through glutamic acid pathways
Starting material/reactant/excipient: compounds used for the initial step of biosynthesis, which are cheap and readily available
Intermediate: products that are formed within the biosynthesis pathways, which can further be processed to make final products, or can, themselves, be utilized as a final product
Final product/product/end product/compounds of interest: cannabinoids, terpenoids, stilbenoids, flavonoids, phenolic amides, lignanamides, spermidine alkaloids, and phenylpropanoids
In-vivo: inside the cell
In-vitro: outside the cell
BAC: bacterial artificial chromosome, carrier of DNA of interest into host
YAC: yeast artificial chromosome, carrier of DNA of interest into host
Vector/cosmid/phage: carrier of DNA of interest into host
Starting Materials All biological organisms produce organic molecules that are processed in many different processes in the organism. The present invention utilizes starting materials that are either:

1) Readily available and relatively pure
2) Cheap to produce or buy
3) Easily modified (via enzymes, catalysts, or other methods)

Based on the above criteria, there are multiple groups and families of compounds that would fit one or all three of the above criteria. These groups and families of compounds include, but are not limited to: ligno-cellulosic biomass, forest biomass, energy/food production waste, commonly available sugar-based substrates, food and feed grains.

Sugars and metabolic intermediates from cellular processes can be used as starting materials. Sugars can be found in abundance in many substances, including, but not limited to the following: rice, soya/rape, cereals (maize), wheat, beans, sugar beet (sugar cane), plant biomass (wood), grasses, and various other sources. Starch, cellulose, fructose, ethanol, and saccharose in the aforementioned substances can be enzymatically converted to glucose, which, after filtration and purification steps, can be used as a raw material for the final products.

Subsequent steps can also be performed on the lignocellulose, which further makes hemicellulose and cellulose, both which make glucose. An advantage of this method is that there are by-products generated which can be sold as raw material to make hydrocarbons, biogas, and other fuel sources. Whole crops or parts of crops, or waste matter from crop products can be used and incorporated into this system, yielding an "eco-friendly" facility. Products made from these raw materials can use any of the starting materials listed in Table 2.

Within the realm of readily available non-biomass/crop bulk material, HFCS (high fructose corn syrup) is a cost effective syrup made with fruit sources that contains anywhere from 30-90% fructose, along with some other sugars. Plants that make molasses, HFCS, and other sugars can be genetically modified to enhance the production of sugar, leading to better yields of starting material from the crop. Other products from these plants can also be incorporated into compounds of interest production via slight system modification. Biodiesel, ethanol, glycerol, lactic acid, whey and glucose are a few others. These work due to the fact that any of these products can be converted into starting material for our own purposes using enzymatic or physiochemical tools.

Plants also have their own innate levels of metabolites that can be harvested into the process from a plant biomass source. Processes can be crafted that utilize most of the metabolites and biomass for API production giving the maximum efficiency and usability per amount of starting material used. (Enzyme combinations or chambers that utilize most intermediates, sugars, oils, etc. in each biomass load).

Biorefineries can be custom designed that cater to specific raw material (plant biomass for harvesting lignocellulose which is further processed and refined into a simple carbohydrate used in the API manufacturing processes). During certain steps throughout the process, thermochemical and other processing can be used for higher efficiencies which are not possible with biochemical processing alone.

Another group of cheap starting materials is agricultural residue, grass, aquatic biomass, and water hyacinth. Products such as oils and alcohols can be made with these bulk materials. These materials can be converted enzymatically and chemically into starting materials that can readily by injected into our API production system.

Specifically, biorefineries can be designed to be extremely efficient, using all parts of the raw material. For example, concerning plant biomass, the biomass can be step-wise processed so we are able to harvest all individual components. The first step can be using solvent to extract terpenes, alkaloids, etc. Other methods can be used to extract steroids, triglycerides, and other valuable metabolites. Finally the biomass can be treated with cellulases to give glucose, which is one of the primary raw materials of choice.

Production Roadmap Summary

The present invention is a method that covers the biosynthesis of hundreds of compounds, mainly found in the *Cannabis* plant. The starting material for these compounds can be any biological compound that is used/produced in a biological organism from the sugar family starting materials or other low cost raw materials processed via enzymes or within organisms to give final products. Information related to the starting materials were detailed in the previous section.

Most sugars and related compounds can be inter-changed using various enzyme systems. For example, we can convert glucose to fructose using Fructose 6-Phosphate (F-6-P) as an intermediate.

Apart from starting materials, we can either:
1) Make enzymes via vectors in bacteria (e.g. *E. coli*) or yeast (e.g. *S. cerevisiae*), extract enzymes, and create in vitro models for making cannabinoids.
2) Make enzymes via protein synthesizing systems (Protein Synth. Robot, Cell Free Expression Systems, etc.)
3) Make final products (compounds of interest) in bacteria or yeast via vectors, plasmids, cosmids, mRNA, various RNA, etc; feed them substrate and purify product.
4) Genetically engineer strains of bacteria and yeast that specialize in cannabinoid production, or intermediate production, or substrate production, etc.
5) Use organic chemistry for certain parts of the above processes.
6) Use various plant starting material for large quantities of substrates or intermediates.
7) Genetically engineer various plants to produce cannabinoids. (e.g. Tomatoes or celery that naturally produce cannabinoids, or algae that produces cannabinoids)
8) Using bioengineered or unengineered *C. sativa* or any other plant/algae cell lines for enzyme/substrate/intermediates/product(s) production.
9) Protein engineering on the various proteins involved in the processes; engineering will enhance the functionality, ruggedness, and efficiency of the enzymes, and altering them into a novel protein, one not found to be covered in any of the above prior art patents.
10) Genetically engineer various plant species to produce higher yielding raw material (sugars) to be used in production of the products. A possibility is to have an indoor/grow for different plants to be used as raw material producers.

After the final product is made, a purification system will filter and concentrate the target molecules. Examples include large scale filtration systems such as chromatography. Once a pure product, we can utilize liquid solutions, caps, sprays, and other delivery systems.

As many of these final products are made, their applications can be seen from glaucoma to cancer, or general well-being. Certain cofactors can be combined with certain final products for more efficacy against specific medical conditions (e.g. combine certain vitamins or other therapeutic compounds with certain compounds of interest). We can also make final products that have certain combinations of compounds of interest with other cofactors as well (e.g. combine THCA/CBDA/Vitamin C, or CBDVA/CBD). This patent covers all the products above and also ones discovered in the future based on the same principles and methods.

DETAILED DESCRIPTION OF THE FIGURES

Referring now to the invention in more detail, in FIG. 1 there is shown a family of sugars and other common derivatives. Along each arrow for each reaction, the number denotes a specific enzyme that catalyzes the reaction. Starting with any sugar in FIG. 1 (list of starting materials in Table 1), we can convert it to glucose to incorporate it into the reaction using the appropriate enzyme, as known to those skilled in the art. An unlimited number of ways are possible when dealing with any starting material, as described above. Enzymes needed for each kind of substrate can be made in vivo or in vitro just as we will be doing for the enzymes in the final product or intermediate production. The final sugar that enters our mechanism will be either glucose or fructose. Through the glycolysis pathway, the sugar will be converted into Acetyl-CoA with the addition of ATP and CoA (shown in FIG. 1). From this point on, the intermediate can follow a variety of paths that can lead to hundreds of products. There are many alternative ways of doing this. We can use the DOX, MEP or MVA pathways to get IPP and DMAPP, which give us GPP and NPP. For a reaction with Olivetolic Acid or Divarinolic Acid, we get many cannabinoids as final products.

The generalized pathway for the production of cannabinoids once the starting material is converted to glucose is the following, using appropriate enzymes as known by those skilled in the art:

Glucose→Fructose→F-6-P→F1:6BP→3-P-Glyceraldehyde→1,3-BPG→3PGA→2-PGA→PEP→Pyruvate→Acetyl-CoA→Acetoacetyl CoA→HMG-CoA→MVA→Mevalonic Acid→Mevalonate-5-P→Mevalonate-5-PP→Isopentyl-5-PP→Dimethylallyl-PP→NPP/GPP→GPP This general pathway is outlined in FIG. 1. From this point on, the pathway can utilize Olivetolic Acid or Divarinolic Acid with GPP, yielding CBGA or CBGVA, which can further yield other cannabinoids, as shown in FIG. 2.

The pathways for stilbenoids, phenylpropanoids, and flavonoids work in a similar fashion. Phenylalanine is generated from sugars, which is then further processed into other compounds using enzymes to final compounds, as shown in FIG. 3 and FIG. 4.

Phenolic amides and lignanamide pathways are derived from tyramine molecules reacting with other compounds, as shown in FIG. 5. Tyramine can also be synthesized in our cells of interest as most living organisms contain the pathway to synthesize tyramine on their own. Same is the case for spermidine alkaloid production, as most cells already produce glutamic acid, which can be further processed by enzymes into the final components, as shown in FIG. 6.

FIG. 7 is the total pathway overview, showing how all the different classes of compounds can be made, and the general paths they take for being biosynthesized in the cell.

Overview of Procedure

A general scheme of the work flow is as follows:

1) Regular/modified/synthetic gene(s) of select enzymes are processed and inserted into an expression system (vector, cosmid, BAC, YAC, phage, etc.) to produce modified hosts.
2) Mod host is then optimized for efficient production and yield via manipulation, silencing, and amplifying inserted or other genes in the host, leading to an efficient system for product. It is important to remember that every organism is different, and to get a specific compound each optimization will also be different.
3) Mod host can produce enzymes and final products/intermediates, or be further modified using host engineering techniques. (Host engineering Can also be performed before insertion of exp. System)
4) Mod and engineering hosts produce products and intermediates.
5) Product is purified and can be further modified/processed.

In Table 1, different final products are listed along with possible uses. This list is by no means exhaustive, and as such this patent covers any molecules that are made this way. Table 2 lists all possible starting materials that can be utilized for a cheap and efficient biosynthesis.

In more detail, referring to the inter-conversion of sugars, we employ enzymes readily available in the market. Pure enzyme stock can be diluted and added to a solution with the substrates. Once the reaction is complete, we can filter out the enzyme via dialysis tubing, by precipitation out of the solution, chromatography, or other industrial methods for filtration and purification. Each step in FIGS. 1 to 7 will give work with this strategy, leading us up to the final products or key intermediate molecules. Certain steps in the process can be worked on by using chemical and physical methods as well. For example, prenylation of certain compounds can be done outside the cell, as it may be advantageous to do so since unprenylated compounds are also high value compounds. Small batches can be prenylated accordingly to demand via a chemical process.

There are also commercially available cell free expression systems, which are able to produce proteins without the need of any host. With appropriate optimization steps, it is possible to get a cheap and efficient process for production of these compounds using identified starting molecules.

Application Techniques

Referring to bacterial, yeast, plant, and algae incorporation of genes, there are a number of strategies that can be applied to achieve this. We can:

1) Add genes for 1-10 enzymes in various commercially available vectors, cosmids, plasmids, etc. Only need 1-10 enzymes added, as others are already built in most living organisms. For example, glycolysis pathway and related enzymes are already present in most hosts.
2) Bioengineer genes for better yield and suitability in the host.
3) Bioengineer strains of bacteria and yeast that are specialized in producing important molecules. Many metabolic strategies exist, with identification by appropriate screening methods:
   1) Rational metabolic engineering: engineering pathways using available information
   2) Evolutionary engineering: using random genetic perturbations and/or mutations (via random mutagenesis in whole genome and/or parts)
   3) Transposon mutagenesis & gene overexpression libraries: overexpression and/or deletion of single or multiple genes;
   4) Global transcription machinery engineering: basal transcription factors mutagenesis causing a global reprogramming of gene transcription and/or translation One strategy is to suppress any pathway that is not essential to our goals or the survival of the host. Another is to enhance our key pathways, or mixing and matching the two methods. The second strategy is through rapid directed evolution, possible by producing many generations so eventually we get a generation of host that has evolved with our genes/functions of interest.
4) Bioengineer custom basic life forms that are specifically making our products, using another organism or using synthetic/modifications. Components from other hosts and system to make a custom organism.
5) Bioengineer bacteria and yeast to have enzyme genes in their chromosomes, and make intermediates or final products inside the host. The product of this process can further be modified.
6) Propagate various colonies of organisms which co-exist symbiotically, with the first making our starting material after utilizing a precursor, and the other colonies making our final product. This process can also be incorporated into an ecosystem type setup of different chambers, each holding different organisms that use specific parts of the raw material to produce intermediates or final products that can be modified post-manufacturing.

Referring to the extraction of enzymes once they have been produced in the host, there are many ways to isolate and purify our enzymes. Many organisms have the ability to excrete proteins, which can be collected much easier than cell lysis, as known by those skilled in the art. This technique is the preferred method.

Another method is to lyse the host culture and purify with traditional biochemistry methods (gels, centrifugation, ammonium sulfate precipitation, etc.), use a specialized nickel column with a prep HPLC (need to add a HIS tag to our proteins; remove HIS tag after purification), etc.

Example 1 (Bacterial)

Bacteria (*E. Coli*, etc.) are inserted with exp. system giving us a modified host. The mod host can either be further processed or it can generate products. Products/intermediates are made in the host, and may be either enzymes that are further extracted and used in vitro, or we add substrates into the bacterial culture so they use the enzymes produced in them to make the substrate. Either way (protein or prod production), purification is carried out to get final products, or intermediates that can be further processed in vitro to give final products. Throughout this procedure, host engineering can be carried out at any step of any process to get better yields.

Example 2 (Plants)

Plant tissue can be used as a starting material to get a tissue culture going. Appropriate expression vectors/systems carry our interest genes into the cells. Alternatively, cell engineering can lead to many combinations that may have similar or different outcomes. The culture can be grown into full plants, and products are ingested by consuming the plants (e.g. tomatoes with certain cannabinoids produced within, etc.). The second way uses the cell culture in a synthetic environment to produce final products/intermediates. Finally, product is purified and used.

Example 3 (Algae)

Algae are modified with the usual techniques used for host engineering. Once completed, the mod host can be embedded into a system similar to biofuel production from algae. Using sunlight and some nutrients, the algae produces final products/intermediates, which is appropriately filtered from the bulk. Other products generated can be further processed to get biofuels or other important compounds that can readily be sold in the market.

Example 4 (Fungi)

Fungi modified with the techniques can:
1) Use plastic to produce final products/intermediates. Plastic needs to be processed and broken down into components before being used in this process via chemical and biological processes, known by those skilled in the art.
2) Clean up waste, whilst producing final products/intermediates at the same time.
3) Produce beer and wine with fungi that also makes final prod/intermediates. Beer and wine will contain our compounds of interest.
4) Use fungi cultures to produce compounds of interest.
5) Genes for *S. cerevisiae* strains to be modified for better yields of final products:
   tHMGR
   upc2-1 (allows higher uptake of exogenous sterol fivefold from medium)
   ERG genes (ERG6, ERG2, ERG3, ERG1, ERG11, ERG24, ERG25, ERG9, ERG10, ERG13, ERG12, ERGS, ERG19, ERG20)
   HMGR1 and HMGR2
   IDI genes
   Gal80p
   DPP1, ADH2, and ALD6 genes
   FPP/GPP synthase (chose avian FPP synthase as it exhibits higher catalytic turnover rates and lower Kms for substrates than other prenyltransferases)
Manipulation, deletion, overexpression, and other modifications to the genes listed above will produce strains that are highly efficient for the production of our compounds of interest. These strains have an exogenous sterol uptake, as the internal sterol pathway has been disabled by manipulations so that all the carbon flux can be directed toward the production of our compounds of interest. Example of genetic pathway regulation in yeast is shown in FIG. 8.

Our initial strategy in *S. cerevisiae* was to increase the carbon flux of our pathways of interest, while decreasing or eliminating pathways that led carbon flux away from our pathways as well. We also focused on exogenous sterol uptake for higher production and secretion levels, cell permeability for more efficient and cheaper production, along with focusing the pathways on utilizing the cheapest sugars. Dynamic control over ergosterol regulation can increase yields as well. Overall result is a strain that is has increased yield many fold, while making the overall production more stable and cheaper.

1) Perform EMS mutagenesis on yeast strains (BY4741, BY4742, CEN.PK, CEN.PK2, EPY300) to get colonies with a SUE (sterol uptake exogenous) mutation. This enables us to provide exogenous sterol to the yeast while cancelling out the gene that diverts carbon flux towards ergosterol, thereby increasing total carbon flux. Without the SUE mutation, the cell diverts lots of carbon flux toward manufacturing sterols, thereby diverting the pools of intermediates away from our compounds and interest leading to very low yields.
2) Perform ERG1 and ERG9 gene knockouts. ERG1 knockout stops the activity of conversion of squalene to squalene epoxide, thereby complementing the SUE mutation and allowing higher uptake of exogenous ergosterol, while ERG9 knockout takes out the cells ability to divert carbon flux towards other metabolites.
3) On some lines, we can perform a DPP1 knockout. DPP1 knockout ensures that FPP/GPP are not converted to FOH, thereby blocking the pathway towards FOH products in the cell.
4) Perform ERG2, ERG3, or ERG6 mutations in different cell lines, while performing upregulation mutation on upc2-1 gene (general transcription factor) on all three lines. This helps increase cell membrane permeability for better excretion of our compounds without the need for cell lysis and having the ability to use two-phase or continuous fermentation. This also allows the cells to uptake more fatty acids, thereby increasing the yield many fold.
5) Overexpression of ERG10, ERG13, HMGR1/2 or tHMGR, ERG12, ERGS, IDI1, HFA1 genes in yeast inserted via vectors. By overexpression of these genes, we are amplifying the enzymes of the MVA pathway from the sugars to our compounds, thereby amplifying the intermediates and final products.
6) Modification of avian and/or *Salmonella* ERG20 gene encoded FPP synthase (ERG20p). Some cells lines can also be modified using the Erg20p(F96C) mutations. This allows for higher Kms and increased catalytic turnover compared to endogenous GPP synthase, while the engineering itself allows for production of GPP.
7) Gal80p gene deletion so we do not need to use galactose sugar when inducing promoter expression. This is important since others have used galactose promoters, which need expensive galactose sugars for production. By deleting this gene, the cells bypass the need for galactose to express enzymes, leading to cheaper and more efficient biosynthesis.
8) Adding ADH2p promoter to induce strong transcription under conditions with low glucose. This promoter is more efficient than the GAL promoter, and has best results while using non-glucose sugars (ethanol, fructose, etc.) which are cheaper.
9) On some lines, we also overexpress ADH2 and ALD6 genes, along with overexpression of an acetyl-CoA C-acetyltransferase to increase efficiency of the system, while also gaining the ability to convert ethanol to acetate efficiently.
10) Adding and overexpressing enzymes for the production of CBDA (OS-OAC fusion enzyme, CsPti, CBDA Synthase), constructed in a single vector. These enzymes are codon optimized.

11) Grow colonies while adding free fatty acids, and hexanoic acid (for THCA, CBDA, CBGA, CBCA) or butyric acid (for THCVA, CBDVA, CBGVA, CBCVA).
12) For production of THCA/THCVA, use THCA synthase in step 10 instead of CBDA synthase. For production of CBGA/CBGVA, follow step 10 but don't use CBDA synthase in vector construct. For production of CBCA/CBCVA, use CBC synthase in step 10 instead.

Our strategy for *Pichia pastoris* (*Pichia* Pink 1, 2, 3 from Invitrogen) yeast was similar to *S. cerevisiae*, except for the following differences:
1) Each enzyme, vector, and primer were optimized for insertion into *Pichia* cells instead of *S. cerevisiae*.
2) Methanol is used to supplement cells in addition to free fatty acid, hexanoic acid, and butyric acid, thereby reducing the total cost of production many fold, while eliminating any contamination issues from other species.
3) No EMS mutagenesis is performed.
4) Knockouts of pep4 (encoding Proteinase A), prb1 (encoding Proteinase B), and YPS1 genes are also introduced. These knockouts allow for the integration of high copy plasmids leading to higher yields.
5) Steps 7, 8, and 9 from the *S. cerevisiae* strategy above are not to be performed in *Pichia* cells.

Example 5 (Cell Free Expression Systems)

Vectors are introduced into cell free expression systems, and make either enzymes or intermediate/final products. Further processing or steps are needed to get purified final products.

Procedures

EMS Mutagenesis (*S. cerevisiae*; BY4741, BY4742, CEN.PK, CEN.PK2, BY300)
1) Cells incubated overnight @ 30 C in 5 mL TPD medium while shaking @ 200 rpm to establish 200 mL YPD shake flask culture.
2) When OD600 of yeast culture reaches 1.0, cells are spun down by centrifugation (12 mins at 4,000 g), washed twice with 20 mL 0.1M sodium phosphate buffer, pH7.0.
3) Cells concentrated by centrifugation again, re-suspended in 1 mL 0.1M sodium phosphate buffer, transferred to 30 mL FALCON tubes, treated with 300 uL EMS (1.2 g/mL).
4) Cells are incubated at 30 C for 1 hr while shaking.
5) Stop mutagenesis by adding 8 mL of sterile 5% sodium thiosulfate to yeast cells.
6) Cells are pelleted, washed with 8 mL sterile water, concentrated by centrifugation, re-suspended in 1 mL sterile water and 100 uL aliquots plated into YPD-NCS agar plate (YPD+50 mg/L each of cholesterol, nystatin, sqalestatin, and 2% Bacto-agar).
7) In some instances, washed cells were resuspended in 1 mL YPDE liquid media for overnight recovery before plating to YPD-NCS agar medium.
8) Incubate cultures for up to two weeks at 30 C until distinct colonies are visible.

Bacteria & Yeast Culturing
1) Grown using standard culture practices.
2) YPD media without selection consisted of 1% Bacto-yeast extract, 2% Bacto-peptone, and 2% glucose.
3) Add 40 mg/L ergosterol to YPD media to get YPDE media.
4) Add 40 mg/L each of nystatin, cholesterol, and squalestatin to YPD media to get TPDNCS media.
5) Add 40 mg/L each of ergosterol and squalestatin to YPD media to get YPDSE media.
6) Prepare minimal media, SCE (pH5.3), by adding 0.67% Bacto-yeast nitrogen base (without amino acids), 2% dextrose, 0.6% succinic acid, 0.14% Sigma yeast dropout soln (-his, -leu, -ura, -trp), uracil (300 mg/L), L-tryptophan (150 mg/L), L-histidine (250 mg/L), L-methionine (200 mg/L), L-leucine (1 g/L), and 40 mg/L of ergosterol.
7) Cholesterol and ergosterol stocks are 10 mg/mL in 50% Triton X-100, 50% ethanol and kept at −20 C.
8) Selection media prepared similarly except without supplementation of media with indicated reagent based on the yeast auxotrophic markers.
9) All solid media plates are prepared with 2% Bacto-agar.

Yeast Transformation & Culture Performance
1) Used FROZEN-EZ Yeast Transformation II Kit from Zymo Research, Orange, Calif., according to manufacturer's recommendations.
2) 1 ug of plasmid was used per transformation, followed by selection on agar plates of SCE medium lacking specified amino acids for auxotrophic markers, or YPDE containing 300 mg/L hygromycin B for screening erg9 knockout at 30 C.
3) Colonies are picked and used to start 3 mL cultures in minimal media to characterize their terpene production capabilities. (6 days incubation at 30 C while shaking)
4) Best cultures are chosen to move further, using 30 mL shake flask cultures.
5) Cultures are grown to saturation in minimal media, inoculated into 30 mL SCE media and 1 mL aliquots are taken out daily for 15 days.
6) Cell growth is monitored via change in optical density at 600 nm every two days using dilutions at later stages of growth.
7) Production of terpenes is determined via testing.

ERG9 Knockout Mutations
1) Primers ERG9PS1 (SEQ ID NO: 1) and ERG9-250downS2 (SEQ ID NO: 2) used to amplify hygromycin resistance gene, hphNT1, from the pFA6-hph-NT1 vector.
2) Simulataneously add 42 bp nucleotide sequences homologous to regions surrounding ERG9 gene in yeast genome.
3) Purified PCR fragment is transformed into various cell lines identified in phase 2 with the ability to accumulate farnesol and selected on YPDE plates containing 300 mg/L hygromycin.
4) Independent single colonies are picked for ergosterol dependent test, PCR confirmation of recombination with hphF (SEQ ID NO: 3) and ERG9 450DWR primer (SEQ ID NO: 5).
5) Farnesol production analysis done by GC-MS/LC-MS.

ERG1 Knockout Mutations
1) Primers ERG1F (SEQ ID NO:12) and ERG1R (SEQ ID NO: 13) used to amplify the sqalene epoxidase synthase ERG1 gene by using Takara high fidelity Primerstar taq polymerase.
2) Obtained PCR fragment is gel purified, A tailed and ligated into the pGEM-Teasy vector.
3) Obtained vector is used as template to run second PCR with primers Erg1-splitF (SEQ ID NO: 14) and EGR1-splitR (SEQ ID NO: 15) to obtain PCR fragment with deletion of 891 bp CDS in the middle, yet containing 310 bp at 5' end region and 291 bp at 3' end region of ERG1 gene which are the target homologous recombination sequence for ERG1 knockout.
4) After digestion with BamHI, self-ligation, and transformation to DH5alpha competent cells, resulting vector is pGEM-ERG1-split.
5) Padh-Kanmx4-Tcyc-LoxP antibiotic selection marker cassette is constructed by assembly PCR of three fragments.
6) Padh promoter is PCR amplified with Padh-loxP-ManHIF (SEQ ID NO: 22) and Padh-Kanmx4R primers (SEQ ID NO: 24) using Yep352 vector as a template.
7) Kanmx4 selection gene is PCR amplified using Padh-kanmx4F (SEQ ID NO: 23) and Tcyc-kanmx4R (SEQ ID NO: 25, SEQ ID NO: 26, and SEQ ID NO: 26) primers using PYM-N14 plasmid as a template.
8) Tcyc terminator was PCR amplified with Padh-loxP-BamHIF (SEQ ID NO: 22) and Padh-Kanmx4R (SEQ ID NO: 24) primers using Pesc vector as a template.
9) 3 PCR fragments containing homologous regions with each other were gel purified and 250 ng of each fragment were mixed together to serve as template for the secondary assembly PCR reaction to yield pAdh-Kanmx4-Tcyc-LoxP cassette.
10) Cassette is digested and inserted into pGEM-ERG1-split vector, and used as template to run PCR with ERG1F and ERG1R to get PCR fragment used to generate cell lines.
11) Pgpd-tHMGR-Tadh fragment was amplified from Pesc-Gpd-leu-tHMGR vector with primers GPD-BamHIP (SEQ ID NO: 28) and Tadh-XhoIIR (SEQ ID NO:29).
12) Insert fragment into pGEM-ERG1-split vector containing kanmx4 cassette.
13) Use construct as template to amplify with ERG1F and EGR1R primers to gain the fragment for building slightly different cell lines, which include integration of one copy of tHMGR into the ERG1 gene.

| Primer name | Primer Sequence |
|---|---|
| ERG9pS1 (SEQ ID NO: 1) | GTACATTTCATAGCCCATCTTCAACAACAATACCGACTTACCCGTACGCTGCAG GTCGAC |
| ERG9 250dwS2 (SEQ ID NO: 2) | CAGATTGACGGAGAGAGGGCCACATTGTTTGTCGGCAATAAATCGATGAATTCG AGCTCG |
| Hph F (SEQ ID NO: 3) | ATGGGTAAAAGCCTGAACTCA |
| Hph R (SEQ ID NO: 4) | TTATTCCTTTGCCCTCGGACGAG |
| ERG9 450dwR (SEQ ID NO: 5) | AGATGCTAGTCAATGGCAGAAG |
| ERG9p300upF (SEQ ID NO: 6) | TGCTTACACAGAGTGAACCTGC |
| ERG9 300R (SEQ ID NO: 7) | CTCGTGGAAGTGACGCAAC |
| pGPD-BamHI F (SEQ ID NO: 8) | cgGGATCCagtttatcattatcaatactcgcc |
| pGPD-NotIR (SEQ ID NO: 9) | gggGCGGCCGCgagctcagtdatcattatc |
| tHMGR-NotIF (SEQ ID NO: 10) | GGGGCGGCCGCAAAACAATGTTGTCACGACTTTTCCGTATGC |
| tHMGR-SpeIR (SEQ ID NO: 11) | GACTAGT TCAAGCTGACTTCTTGGTGCACGTTCCTTG |
| ERG1F (SEQ ID NO: 12) | ATGTCTGCTGTTAACGTTGCACCTG |
| ERG1R (SEQ ID NO: 13) | TTAACCAATCAACTCACCAAAC |
| ERG1-split F (SEQ ID NO: 14) | CGGGATCCCTCGAG TTGTTCGCTGCTGACAGCGATAAC |
| ERG1-splitR (SEQ ID NO: 15) | CGGGATCCGCTAGCGGTACCACATGGGTCCTTTATATTGACACG |
| ERG1 90up F (SEQ ID NO: 16) | ATCAGAACAATTGTCCAGTATTG |
| ERG1100dwR (SEQ ID NO: 17) | AATGTACTATACAAGCCTTCC |
| bSQS-NotIF (SEQ ID NO: 18) | GGGGCGGCCGCAAAACAATGGGGATGCTTCGCTGGGGAGT |

| Primer name | Primer Sequence |
| --- | --- |
| bSQS-SpeIR (SEQ ID NO: 19) | GACTAGTTTAGCTCCTCAATTCGTCAAAGGT |
| Cre-NotIF (SEQ ID NO: 20) | GGGGCGGCCGCAAAACAATGGACATGTTCAGGGATCGCCAGG |
| Cre-SpeIR (SEQ ID NO: 21) | GACTAGTCTAATCGCCATCTTCCAGCAGGCG |
| Padh-Loxp-BamHIF (SEQ ID NO: 22) | CGGGATCCATAACTTCGTATAGCATACATTATACGAAGTTATGTGGAATATTTC GGATAT |
| Padh-Kanmx4F (SEQ ID NO: 23) | GCATACAATCAACTAAGCTAAGCTAAAACAATGGGTAAGGAAAAGACTCACGTT TC |
| Padh-Kanmx4R (SEQ ID NO: 24) | GAAACGTGAGTCTTTTCCTTACCCATTGTTTTAGCTTAGCTTAGTTGATTGTAT GC |
| Kanmx4-TcycF (SEQ ID NO: 25) | CATTTGATGCTCGATGAGTTTTTCTAAATCCGCTCTAACCGAAAAGGAAGGAG |
| Kanmx4-TcycR (SEQ ID NO: 26) | CTCCTTCCTTTTCGGTTAGAGCGGATTTAGAAAAACTCATCGAGCATCAAATG |
| Tcyc-LoxP-NheIR (SEQ ID NO: 27) | GGGGCTAGCATAACTTCGTATAATGTATGCTATACGAAGTTATCTTCGAGCGTC CCAAAA |
| Gpd-BamHIF (SEQ ID NO: 28) | CGGGATCCAGTTTATCATTATCAATACTCG |
| Tadh-XhoIR (SEQ ID NO: 29) | GGGCTCGAG GAGCGACCTCATGCTATACCTG |
| Kanmx4R (SEQ ID NO: 30) | TTAGAAAAACTCATCGAGCATC |

Expression of Enzymes for Cannabinoid Production

LS 5' FWD
SEQ ID NO: 31
Length: 55
Type: DNA
Organism: Artificial Sequence
Notes: Primer Gcatagcaatctaatctaagttttaaa atgaatcatttgagagcagaagggcctgc

CB 5' FWD

SEQ ID NO: 32
Length: 56
Type: DNA
Organism: Artificial Sequence
Notes: Primer caccagaacttagtttcgacggataaa atggaaaccggtttgtcctcggtttgcac All REV SEQ ID NO: 33
Length: 58
Type: DNA
Organism: Artificial Sequence
Notes: Primer cataactaattacatgatttaaccTTAAACATCAGATTCAATAGAGCCGCCTCCACTG Backbone | CBGA synthase | Flexible spacer | CBD synthase target peptide SEQ ID NO: 34
Length:
Type: DNA
Organism: artificial sequence
Notes: Codon optimized -continued

```
   1 ggttaaatca tgtaattagt tatgtcacgc ttacattcac gccctccccc cacatccgct
  61 ctaaccgaaa aggaaggagt tagacaacct gaagtctagg tccctattta ttttttata
 121 gttatgttag tattaagaac gttatttata tttcaaattt ttcttttttt tctgtacaga
 181 cgcgtgtacg catgtaacat tatactgaaa accttgcttg agaaggtttt gggacgctcg
 241 aaggctttaa tttgcggccc ctcacctgca cgcaaaatag gataattata ctctatttct
 301 caacaagtaa ttggttgttt ggccgagcgg tctaaggcgc ctgattcaag aaatatcttg
 361 accgcagtta actgtgggaa tactcaggta tcgtaagatg caagagttcg aatctcttag
 421 caaccattat ttttttcctc aacataacga gaacacacag gggcgctatc gcacagaatc
 481 aaattcgatg actggaaatt ttttgttaat ttcagaggtc gcctgacgca tatacctttt
 541 tcaactgaaa aattgggaga aaaggaaag gtgagagcgc cggaaccggc ttttcatata
 601 gaatagagaa gcgttcatga ctaaatgctt gcatcacaat acttgaagtt gacaatatta
 661 tttaaggacc tattgttttt tccaataggt ggttagcaat cgtcttactt tctaactttt
 721 cttaccttt acatttcagc aatatatata tatatatttc aaggatatac cattctaatg
 781 tctgccccta agaagatcgt cgttttgcca ggtgaccacg ttggtcaaga atcacagcc
 841 gaagccatta aggttcttaa agctatttct gatgttcgtt ccaatgtcaa gttcgatttc
 901 gaaaatcatt taattggtgg tgctgctatc gatgctacag gtgttccact tccagatgag
 961 gcgctggaag cctccaagaa ggctgatgcc gttttgttag gtgctgtggg tggtcctaaa
1021 tggggtaccg gtagtgttag acctgaacaa ggtttactaa aaatccgtaa agaacttcaa
1081 ttgtacgcca acttaagacc atgtaacttt gcatccgact ctcttttaga cttatctcca
1141 atcaagccac aatttgctaa aggtactgac ttcgttgttg tcagagaatt agtgggaggt
1201 atttactttg gtaagagaaa ggaagatgat ggtgatggtg tcgcttggga tagtgaacaa
1261 tacaccgttc cagaagtgca agaatcaca agaatggccg ctttcatggc cctacaacat
1321 gagccaccat tgcctatttg gtccttggat aaagctaatt ttttggcctc ttcaagatta
1381 tggagaaaaa ctgtggagga aaccatcaag aacgaattcc ctacattgaa ggttcaacat
1441 caattgattg attctgccgc catgatccta gttaagaacc caacccacct aaatggtatt
1501 ataatcacca gcaacatgtt tggtgatatc atctccgatg aagcctccgt tatcccaggt
1561 tccttgggtt tgttgccatc tgcgtccttg gcctctttgc cagacaagaa caccgcattt
1621 ggtttgtacg aaccatgcca cggttctgct ccagatttgc caaagaataa ggtcaaccct
1681 atcgccacta tcttgtctgc tgcaatgatg ttgaaattgt cattgaactt gcctgaagaa
1741 ggtaaggcca ttgaagatgc agttaaaaag gttttggatg caggcatcag aactggtgat
1801 ttaggtggtt ccaacagtac caccgaagtc ggtgatgctg tcgccgaaga agttaagaaa
1861 atccttgctt aaaaagattc tcttttttta tgatatttgt acataaactt tataaatgaa
1921 attcataata gaaacgacac gaaattacaa aatggaatat gttcataggg taacgctatg
1981 atccaatatc aaaggaaatg atagcattga aggatgagac taatccaatt gaggagtggc
2041 agcatataga acagctaaag ggtagtgctg aaggaagcat acgataccc gcatggaatg
2101 ggataatatc acaggaggta ctagactacc tttcatccta cataaataga cgcatataag
2161 tacgcattta agcataaaca cgcactatgc cgttcttctc atgtatatat atatacaggc
2221 aacacgcaga tataggtgcg acgtgaacag tgagctgtat gtgcgcagct cgcgttgcat
2281 tttcggaagc gctcgttttc ggaaacgctt tgaagttcct attccgaagt tcctattctc
2341 tagaaagtat aggaacttca gagcgctttt gaaaaccaaa agcgctctga agtcgcactt
```

-continued

```
2401 tcaaaaaacc aaaaacgcac cggactgtaa cgagctacta aaatattgcg aataccgctt 2461 ccacaaaacat tgctcaaaag tatctctttg ctatatatct ctgtgctata tccctatata 2521 acctacccat ccacctttcg ctccttgaac ttgcatctaa actcgacctc tacattttt 2581 atgtttatct ctagtattac tcttttagaca aaaaaattgt agtaagaact attcatagag 2641 tgaatcgaaa acaatacgaa aatgtaaaca tttcctatac gtagtatata gagacaaaat 2701 agaagaaacc gttcataatt ttctgaccaa tgaagaatca tcaacgctat cactttctgt 2761 tcacaaagta tgcgcaatcc acatcggtat agaatataat cggggatgcc tttatcttga 2821 aaaaatgcac ccgcagcttc gctagtaatc agtaaacgcg ggaagtggag tcaggctttt 2881 tttatggaag agaaaataga caccaaagta gccttcttct aaccttaacg gacctacagt 2941 gcaaaaagtt atcaagagac tgcattatag agcgcacaaa ggagaaaaaa agtaatctaa 3001 gatgctttgt tagaaaaata gcgctctcgg gatgcatttt tgtagaacaa aaaagaagta 3061 tagattcttt gttggtaaaa tagcgctctc gcgttgcatt tctgttctgt aaaaatgcag 3121 ctcagattct ttgtttgaaa aattagcgct ctcgcgttgc attttgttt tacaaaaatg 3181 aagcacagat tcttcgttgg taaaatagcg ctttcgcgtt gcatttctgt tctgtaaaaa 3241 tgcagctcag attctttgtt tgaaaaatta gcgctctcgc gttgcatttt tgttctacaa 3301 aatgaagcac agatgcttcg ttcaggtggc acttttcggg gaaatgtgcg cggaacccct 3361 atttgtttat ttttctaaat acattcaaat atgtatccgc tcatgagaca ataaccctga 3421 tattggtcag aattggttaa ttggttgtaa cactgaccc tatttgttta ttttttctaaa 3481 tacattcaaa tatgtatccg ctcatgagac aataaccctg ataaatgctt caataatatt 3541 gaaaaaggaa gaatatgagc catattcaac gggaaacgtc gaggccgcga ttaaattcca 3601 acatggatgc tgatttatat gggtataaat gggctcgcga taatgtcggg caatcaggtg 3661 cgacaatcta tcgcttgtat gggaagcccg atgcgccaga gttgtttctg aaacatggca 3721 aaggtagcgt tgccaatgat gttacagatg agatggtcag actaaactgg ctgacggaat 3781 ttatgccact tccgaccatc aagcatttta tccgtactcc tgatgatgca tggttactca 3841 ccactgcgat ccccggaaaa acagcgttcc aggtattaga agaatatcct gattcaggtg 3901 aaaatattgt tgatgcgctg gcagtgttcc tgcgccggtt gcactcgatt cctgtttgta 3961 attgtccttt taacagcgat cgcgtatttc gcctcgctca ggcgcaatca cgaatgaata 4021 acggtttggt tgatgcgagt gattttgatg acgagcgtaa tggctggcct gttgaacaag 4081 tctggaaaga aatgcataaa cttttgccat tctcaccgga ttcagtcgtc actcatggtg 4141 atttctcact tgataacctt atttttgacg aggggaaatt aataggttgt attgatgttg 4201 gacgagtcgg aatcgcagac cgataccagg atcttgccat cctatggaac tgcctcggtg 4261 agttttctcc ttcattacag aaacggcttt ttcaaaaata tggtattgat aatcctgata 4321 tgaataaatt gcaatttcat ttgatgctcg atgagttttt ctaactcatg accaaaatcc 4381 cttaacgtga gttacgcgcg cgtcgttcca ctgagcgtca gaccccgtag aaaagatcaa 4441 aggatcttct tgagatcctt ttttctgcg cgtaatctgc tgcttgcaaa caaaaaaacc 4501 accgctacca gcggtggttt gtttgccgga tcaagagcta ccaactcttt ttccgaaggt 4561 aactggcttc agcagagcgc agataccaaa tactgttctt ctagtgtagc cgtagttagc 4621 ccaccacttc aagaactctg tagcaccgcc tacatacctc gctctgctaa tcctgttacc 4681 agtggctgct gccagtggcg ataagtcgtg tcttaccggg ttggactcaa gacgatagtt 4741 accggataag gcgcagcggt cgggctgaac ggggggttcg tgcacacagc ccagcttgga 4801 gcgaacgacc tacaccgaac tgagatacct acagcgtgag ctatgagaaa gcgccacgct
```

```
4861 tcccgaaggg agaaaggcgg acaggtatcc ggtaagcggc agggtcggaa caggagagcg
4921 cacgagggag cttccagggg gaaacgcctg gtatctttat agtcctgtcg ggtttcgcca
4981 cctctgactt gagcgtcgat ttttgtgatg ctcgtcaggg gggcggagcc tatggaaaaa
5041 cgccagcaac gcggccttt tacggttcct ggccttttgc tggccttttg ctcacatgtt
5101 ctttcctgcg ttatcccctg attctgtgga taaccgtatt accgcctttg agtgagctga
5161 taccgctcgg ggtcgtgcag gtagtttatc attatcaata ctcgccattt caaagaatac
5221 gtaaataatt aatagtagtg attttcctaa ctttatttag tcaaaaaatt agccttttaa
5281 ttctgctgta acccgtacat gcccaaaata ggggcgggt tacacagaat ataacatc
5341 gtaggtgtct gggtgaacag tttattcctg gcatccacta aatataatgg agcccgcttt
5401 ttaagctggc atccagaaaa aaaaagaatc ccagcaccaa aatattgttt tcttcaccaa
5461 ccatcagttc ataggtccat tctcttagcg caactacaga gaacaggggc acaaacaggc
5521 aaaaaacggg cacaacctca atggagtgat gcaaccagcc tggagtaaat gatgacacaa
5561 ggcaattgac ccacgcatgt atctatctca ttttcttaca ccttctatta ccttctgctc
5641 tctctgattt ggaaaaagct gaaaaaaag gttgaaacca gttccctgaa attattcccc
5701 tacttgacta ataagtatat aaagacggta ggtattgatt gtaattctgt aaatctattt
5761 cttaaacttc ttaaattcta cttttatagt tagtctttt tttagttta aaacaccaga
5821 acttagtttc gacggataaa atggaaaccg gtttgtcctc ggtttgcact ttctccttcc
5881 aaacaaacta tcatacactc ctgaacccgc acaataacaa tcccaaaact tccctgctgt
5941 gttataggca cccaaagaca ccaatcaaat actcctacaa taactttcca tctaagcatt
6001 gtagcacaaa aagtttccat ttgcaaaata agtgttccga atctctgtcc atcgccaaaa
6061 attccattag ggctgccact actaatcaaa ctgaaccacc agagtctgat aatcattctg
6121 tcgccacaaa gattctgaat tttgggaagg cttgttggaa gttacaaaga ccatatacaa
6161 ttattgcctt tacctcttgt gcctgtggtt tatttggtaa ggaactgttg cataatacaa
6241 atttaatatc ttggtcattg atggaaacgt tcaaagcatt ttttttctta gtcgctatcc
6301 tttgtattgc ttcttttcacc accactatca accagattta cgacttacat attgacagaa
6361 ttaacaagcc agatttgcca ctggcttcgg gcgagatttc cgtcaatact gcctggatca
6421 tggaaacttc tattattgtt gccttgtttg gattgataat caccataaaa atggaaacta
6481 agggtggtcc attgtatatt ttcggttact gttttggtat cttcgggggc atcgtctact
6541 ctgttcctcc attcagatgg aaacaaaatc cttccacagc attcctttg aacttcctgg
6601 cgcacattat aaccaacttt acttttatt atgcctccag agccgccctg gggctgccct
6661 ttgaattacg cccctccttt acatttttac tggccttcat ggagaccaag tccatggaga
6721 ctggttctgc tctcgcgttg atcaaagatg cttccgatgt ggaaggtgac accaaatttg
6761 gtatatccac tttggccagc aagtatggtt ccaggaattt gaccctattt tgttctggta
6841 tcgtgctgct gtcttatgtt gcagccatct tggctggcat catttggcca caggctttca
6901 attcaaatgt tatggagacg ctgctctcgc atgctatttt ggcattttgg ttgattctac
6961 agacaagaga ttttgcttta accaattatg acccagaagc tggtagaaga ttttacgaat
7021 ttatggaaac atgaaaatta tactatgctg aatatttagt gtacgttttc attggggggcg
7081 gctccagcgc cggcggcggc tcttctgcgg gcggttggtc tcatccacaa tttgagaaag
7141 gtgggtcgtc tggcggcggc agcggggggcg ggtccggcgg ggggagcggc ggtatgaaat
7201 gttcgacctt ctctttttgg tttgtctgta aaataatttt ttttttcttc agctttaaca
```

-continued

```
7261 ttcaaaccag cattgcaaat ccaagagaaa atttcttgaa atgcttttca caatatatcc 7321 ccaataatgc tactaacttg aagctagttt atactcaaaa caacccttg tacatgtccg 7361 tgctcaactc caccattcac aacctaagat tcacttcaga cactacccca aaaccattag 7441 ttattgtgac accttctcac gtttcacata tccaaggtac tattttatgc tccaagaagg 7501 tcggcctgca aattagaact agatctggag gtcatgattc agaaggaatg tcttacatct 7561 ctcaagttcc atttgtgatt gtcgatttaa gaaatatgag gagcattaag atcgatgttc 7621 actcccaaac ggcatgggtt gaagccggtg ccaccttggg cgaagtttac tactgggtca 7681 acgagaagaa tgaaaactta tcactagccg caggttattg tccaactgtt tgtgctggtg 7741 gccatttcgg aggcggcggc tacggtcctc taatgagaaa ctacggctta gctgctgaca 7801 atatcatcga cgctcacttg gttaacgttc atggtaaagt tttagataga aaatctatgg 7861 gtgaggatct tttctgggct ttgagaggtg gcggcgcaga atcatttggc attatcgttg 7921 cttggaagat cagattggtg gctgtcccca agtctacaat gttttctgtg aagaaaatta 7961 tggaaatcca tgaattggtc aaactggtga ataaatggca aaacatagct acaagtacg 8041 ataaagactt gctgttaatg acacatttta ttaccaggaa catcactgat aaccaaggca 8101 agaacaagac tgcaattcat acttatttt cctccgtttt tttgggtggt gtcgactccc 8161 tcgtggatct gatgaataaa tcattccctg aactaggtat taaaaaaacc gattgtagac 8221 aattgagttg gattgatacc atcatattct acagtggtgt tgttaattat gatactgaca 8281 acttcaacaa agaaatactg ctggaccgtt ccgccggcca gaatggtgct tttaaaatca 8341 agttggatta tgtgaaaaag cctattccag aatccgtatt tgttcaaata ttggaaaagc 8401 tgtatgaaga agacattggt gcaggcatgt acgctctta tccttatggc ggcataatgg 8461 atgaaatttc tgaaagtgcc attccttcc cacatagggc cgggatcctg tacgagttat 8521 ggtacatttg ttcatgggaa aagcaagaag ataatgaaaa acatttaaat tggataagaa 8561 atatttataa tttatgact ccatacgtct ccaaaaaccc acgcctggca tatttgaatt 8641 acagagacct ggatattggc atcaatgatc ctaaaaaccc aaataattac actcaggcaa 8701 gaatatgggg tgaaaaatat ttcggcaaaa attttgatag gctggtcaag gttaaaacac 8761 tggttgatcc aaacaatttc tttagaaacg aacaatctat cccacctctg cctagacata 8821 gacacggcgg tggaagcagt ggaggcggct ctattgaatc tgatgtttaa tga
```

Backbone | OLS | Flexible spacer | OAC | target peptide

SEQ ID NO: 35
Length:
Type: DNA
Organism: artificial sequence
Notes: Codon optimized

```
  1 ggttaaatca tgtaattagt tatgtcacgc ttacattcac gccctccccc cacatccgct 61 ctaaccgaaa aggaaggagt tagacaacct gaagtctagg tccctatta ttttttata 121 gttatgttag tattaagaac gttatttata tttcaaattt ttctttttt tctgtacaga 181 cgcgtgtacg catgtaacat tatactgaaa accttgcttg agaaggtttt gggacgctcg 241 aaggctttaa tttgcggccc ctcacctgca cgcaaaaagc ttttcaattc aattcatcat 301 ttttttttta ttcttttttt tgatttcggt ttctttgaaa ttttttgat tcggtaatct 361 ccgaacagaa ggaagaacga aggaaggagc acagacttag attggtatat atacgcatat 421 gtagtgttga gaaacatga aattgcccag tattcttaac ccaactgcac agaacaaaaa 481 ccagcaggaa acgaagataa atcatgtcga agctacata taaggaacgt gctgctactc 541 atcctagtcc tgttgctgcc aagctattta atatcatgca cgaaaagcaa acaaacttgt
```

-continued

```
 601 gtgcttcatt ggatgttcgt accaccaagg aattactgga gttagttgaa gcattaggtc
 661 ccaaaatttg tttactaaaa acacatgtgg atatcttgac tgattttcc atggagggca
 721 cagttaagcc gctaaaggca ttatccgcca agtacaattt tttactcttc gaagatagaa
 781 aatttgctga cattggtaat acagtcaaat tgcagtactc tgcgggtgta tacagaatag
 841 cagaatgggc agacattacg aatgcacacg gtgtggtggg cccaggtatt gttagcggtt
 901 tgaagcaggc ggcagaagaa gtaacaaagg aacctagagg ccttttgatg ttagcagaat
 961 tgtcatgcaa gggctcccta tctactggag aatatactaa gggtactgtt gacattgcga
1021 aaagcgacaa agattttgtt atcggcttta ttgctcaaag agacatgggg ggaagagatg
1081 aaggttacga ttggttgatt atgacacccg gtgtgggttt agatgacaag ggagatgcat
1141 tgggtcaaca gtatagaacc gtggatgatg ttgtctctac aggatctgac attattattg
1201 ttggaagagg actatttgca aagggaaggg atgctaaggt agagggtgaa cgttacagaa
2161 aagcaggctg ggaagcatat ttgagaagat gcggccagca aaactaaaaa actgtattat
1321 aagtaaatgc atgtatacta aactcacaaa ttagagcttc aatttaatta tatcagttat
1381 tacccacgct atgatccaat atcaaaggaa atgatagcat tgaaggatga gactaatcca
1441 attgaggagt ggcagcatat agaacagcta aagggtagtg ctgaaggaag catacgatac
1501 cccgcatgga atgggataat atcacaggag gtactagact accttttcatc ctacataaat
1561 agacgcatat aagtacgcat ttaagcataa acacgcacta tgccgttctt ctcatgtata
1621 tatatataca ggcaacacgc agatataggt gcgacgtgaa cagtgagctg tatgtgcgca
1681 gctcgcgttg cattttcgga agcgctcgtt ttcggaaacg ctttgaagtt cctattccga
1741 agttcctatt ctctagaaag tataggaact tcagagcgct tttgaaaacc aaaagcgctc
1801 tgaagtcgca ctttcaaaaa accaaaaacg caccggactg taacgagcta ctaaaatatt
1861 gcgaataccg cttccacaaa cattgctcaa aagtatctct ttgctatata tctctgtgct
1921 atatccctat ataacctacc catccacctt tcgctccttg aacttgcatc taaactcgac
1981 ctctacattt tttatgttta tctctagtat tactctttag acaaaaaaat tgtagtaaga
2041 actattcata gagtgaatcg aaaacaatac gaaaatgtaa acatttccta tacgtagtat
2101 atagagacaa aatagaagaa accgttcata attttctgac caatgaagaa tcatcaacgc
2161 tatcactttc tgttcacaaa gtatgcgcaa tccacatcgg tatagaatat aatcggggat
2221 gcctttatct tgaaaaaatg cacccgcagc ttcgctagta atcagtaaac gcgggaagtg
2281 gagtcaggct tttttttatgg aagagaaaat agacaccaaa gtagccttct tctaaccttta
2341 acggacctac agtgcaaaaa gttatcaaga gactgcatta tagagcgcac aaaggagaaa
2401 aaaagtaatc taagatgctt tgttagaaaa atagcgctct cgggatgcat ttttgtagaa
2461 caaaaagaa gtatagattc tttgttggta aaatagcgct ctcgcgttgc atttctgttc
2521 tgtaaaaatg cagctcagat tctttgtttg aaaaattagc gctctcgcgt tgcatttttg
2581 ttttacaaaa atgaagcaca gattcttcgt tggtaaaata gcgctttcgc gttgcatttc
2641 tgttctgtaa aaatgcagct cagattcttt gtttgaaaaa ttagcgctct cgcgttgcat
2701 ttttgttcta caaaatgaag cacagatgct tcgttcaggt ggcacttttc ggggaaatgt
2761 gcgcggaacc cctatttgtt tatttttcta aatacattca aatatgtatc cgctcatgag
2821 acaataaccc tgatattggt cagaattggt taattggttg taacactgac ccctatttgt
2881 ttatttttct aaatacattc aaatatgtat ccgctcatga acaataaacc ctgataaatg
2941 cttcaataat attgaaaaag gaagaatatg agtattcaac atttccgtgt cgcccttatt
```

-continued

```
3001 cccttttttg cggcattttg ccttcctgtt tttgctcacc cagaaacgct ggtgaaagta 3061 aaagatgctg aagatcagtt gggtgcacga gtgggttaca tcgaactgga tctcaacagc 3121 ggtaagatcc ttgagagttt tcgccccgaa gaacgttttc caatgatgag cacttttaaa 3181 gttctgctat gtggcgcggt attatcccgt attgacgccg ggcaagagca actcggtcgc 3241 cgcatacact attctcagaa tgacttggtt gagtactcac cagtcacaga aaagcatctt 3301 acggatggca tgacagtaag agaattatgc agtgctgcca taaccatgag tgataacact 3361 gcggccaact tacttctgac aacgatcgga ggaccgaagg agctaaccgc ttttttgcac 3421 aacatggggg atcatgtaac tcgccttgat cgttgggaac cggagctgaa tgaagccata 3481 ccaaacgacg agcgtgacac cacgatgcct gtagcgatgg caacaacgtt gcgcaaacta 3541 ttaactggcg aactacttac tctagcttcc cggcaacaat taatagactg gatggaggcg 3601 gataaagttg caggaccact tctgcgctcg gcccttccgg ctggctggtt tattgctgat 3661 aaatccggag ccggtgagcg tggttctcgc ggtatcatcg cagcgctggg gccagatggt 3721 aagccctccc gtatcgtagt tatctacacg acggggagtc aggcaactat ggatgaacga 3781 aatagacaga tcgctgagat aggtgcctca ctgattaagc attggtaact catgaccaaa 3841 atcccttaac gtgagttacg cgcgcgtcgt tccactgagc gtcagacccc gtagaaaaga 3901 tcaaaggatc ttcttgagat ccttttttc tgcgcgtaat ctgctgcttg caaacaaaaa 3961 aaccaccgct accagcggtg gtttgtttgc cggatcaaga gctaccaact cttttttccga 4021 aggtaactgg cttcagcaga gcgcagatac caaatactgt tcttctagtg tagccgtagt 4081 tagcccacca cttcaagaac tctgtagcac cgcctacata cctcgctctg ctaatcctgt 4141 taccagtggc tgctgccagt ggcgataagt cgtgtcttac cgggttggac tcaagacgat 4201 agttaccgga taaggcgcag cggtcgggct gaacggggg ttcgtgcaca cagcccagct 4261 tggagcgaac gacctacacc gaactgagat acctacagcg tgagctatga gaaagcgcca 4321 cgcttcccga agggagaaag gcggacaggt atccggtaag cggcagggtc ggaacaggag 4381 agcgcacgag ggagcttcca gggggaaacg cctggtatct ttatagtcct gtcgggtttc 4441 gccacctctg acttgagcgt cgatttttgt gatgctcgtc aggggggcgg agcctatgga 4501 aaaacgccag caacgcggcc ttttttacggt tcctggcctt tgctggcct tttgctcaca 4561 tgttctttcc tgcgttatcc cctgattctg tggataaccg tattaccgcc tttgagtgag 4621 ctgataccgc tcgggtcgt gcaggtatag cttcaaaatg tttctactcc ttttttactc 4681 ttccagattt tctcggactc cgcgcatcgc cgtaccactt caaaacaccc aagcacagca 4741 tactaaattt ccctctttc ttcctctagg gtgtcgttaa ttacccgtac taaaggtttg 4801 gaaagaaaa aagtgaccgc ctcgtttctt tttcttcgtc gaaaaaggca ataaaaattt 4861 ttatcacgtt tctttttctt gaaaattttt tttttgatt tttttctctt tcgatgacct 4921 cccattgata tttaagttaa taaacggact tcaatttctc aagtttcagt ttcattttc 4981 ttgttctatt acaactttt ttacttcttg ctcattagaa agaaagcata gcaatctaat 5041 ctaagtttaa aatgaatcat ttgagagcag aagggcctgc ttccgtgctg gctattggta 5101 ccgccaatcc agaaaatatc ctgctgcagg acgaattccc agattactat tttagggtca 5161 ccaaatctga acatatgaca caattgaaag agaaattcag aaagatttgt gacaagtcca 5221 tgattaggaa aagaaattgt ttttgaatg aagaacactt gaagcaaaat cctcgcctgg 5281 tggagcatga aatgcaaact ttggatgcta gacaagacat gttggtggtg gaagttccaa 5341 agctggggaa ggatgcctgt gccaaggcca ttaaagaatg gggccaacca aaatccaaaa 5401 ttacccacct gattttcacc tccgcctcca ccactgatat gccaggtgca gactatcatt
```

```
5461 gtgctaaatt gttgggtttg tcccctccg tgaagagagt tatgatgtat caattaggtt 5521 gttatggcgg cggcaccgtt ctgagaattg ccaaagacat tgctgaaaac aataaaggtg 5581 cgcgcgtttt ggctgtttgt tgtgatatta tggcatgttt atttagaggt ccaagtgaaa 5641 gtgacttgga attgctagtg ggccaggcca tatttggtga tggtgccgct gctgtgatcg 5701 ttggtgctga gcctgatgaa tctgtcggtg aaagaccaat ttttgaactg gtttccactg 5761 gtcaaaccat tttgccaaat tcagaaggta ctattggcgg ccatatcaga gaagctggtt 5821 taatctttga tttgcacaag gatgtcccaa tgttaatttc caataatatt gaaaaatgtt 5881 tgatcgaagc atttaccccc atcggtattt ctgattggaa ttccatcttc tggattacac 5941 atcctggcgg taaagctatc ttagataaag ttgaggagaa gttgcattta aagtctgaca 6001 aatttgttga ttcaagacat gtcctgtctg agcacggtaa tatgtcttcc tcgaccgtct 6061 tgtttgtcat ggatgagttg aggaagaggt ccctggaaga aggcaagagc accaccggtg 6121 acggttttga gtgggggtc ctctttggat tgggccagg cctgaccgta gaaagggttg 6181 ttgtccgctc ggtgccaatc aaatatggtg gggggtccag cgccggtggc gggagctccg 6241 cgggcggttg gtctcaccca caatttgaaa agggtggcag cagcggcggc ggctctggcg 6301 gaggctccgg cggggctcg gggggtatgg ctgtcaagca tctgatcgtg ctgaagttca 6361 aagatgaaat tactgaagcc caaaaggagg aattttttcaa gacatatgtt aatttggtta 6421 acatcattcc agcaatgaaa gatgtttatt ggggtaagga cgttactcaa aaaataagg 6481 aagagggtta cactcatatt gttgaagtca ctttcgaatc cgtcgaaaca attcaagatt 6541 atattattca tccagctcat gttgggtttg gcgatgtgta cagatcattt tgggaaaaat 6601 tattgatttt tgactacaca ccaagaaaag gcggtggaag cagtggaggc ggctctattg 6661 aatctgatgt ttaatag
```

Overexpression of ERG8m HFA1, ERG 10, ERG13, tHMGR, HMGR, ERG12, ERG8, IDI Genes (for higher levels of intermediates)
Same process as expression of Synthase expression, but with 3 copies expressed in yeast cells.
Backbone | GGPS1| 2a protease | HMC-CoA reductase| flexible spacer IDI1
SEQ ID NO: 36
Length:
Type: DNA
Organism: artificial sequence
Notes: Codon optimized

```
  1 atggagaaga ctcaagaaac agtccaaaga attcttctag aaccctataa atacttactt 61 cagttaccag gtaaacaagt gagaaccaaa ctttcacagg catttaatca ttggctgaaa 121 gttccagagg acaagctaca gattattatt gaagtgacag aaatgttgca taatgccagt 181 ttactcatcg atgatattga agacaactca aaactccgac gtggcttcc agtggcccac 241 agcatctatg gaatcccatc tgtcatcaat tctgccaatt acgtgtattt ccttggcttg 301 gagaaagtct taaccttga tcacccagat gcagtgaagc tttttacccg ccagcttttg 361 gaactccatc agggacaagg cctagatatt tactggaggg ataattacac ttgtcccact 421 gaagaagaat ataagctat ggtgctgcag aaaacaggtg gactgtttgg attagcagta 481 ggtctcatgc agttgttctc tgattacaaa gaagatttaa aaccgctact taatacactt 541 gggctctttt tccaaattag ggatgattat gctaatctac actccaaaga atatagtgaa 601 aacaaaagtt tttgtgaaga tctgacagag ggaaagttct catttcctac tattcatgct 661 atttggtcaa ggcctgaaag cacccaggtg cagaatatct gcgccagag aacagaaaac 721 atagatataa aaaatactg tgtacattat cttgaggatg taggttcttt tgaatacact 781 cgtaataccc ttaaagagct tgaagctaaa gcctataaac agattgatgc acgtggtggg
```

-continued

```
 841 aaccctgagc tagtagcctt agtaaaacac ttaagtaaga tgttcaaaga agaaaatgaa
 901 ggcggttctg gcagcggaga gggcagagga agtcttctaa catgcggtga cgtggaggag
 961 aatcccggcc ctaggtctgg cagcggagag ggcagaggaa gtcttctaac atgcggtgac
1021 gtggaggaga atcccggccc taggacacaa agaaagtcc cagacaattg ttgtagacgt
1081 gaacctatgc tggtcagaaa taaccagaaa tgtgattcag tagaggaaga gacagggata
1141 aaccgagaaa gaaaagttga ggttatataa cccttagtgg ctgaaacaga taccccaaac
1201 agagctacat ttgtggttgg taactcctcc ttactcgata cttcatcagt actggtgaca
1261 caggaacctg aaattgaact tcccagggaa cctcggccta atgaagaatg tctacagata
1321 cttgggaatg cagagaaagg tgcaaaattc cttagtgatg ctgagatcat ccagttagtc
1381 aatgctaagc atatcccagc ctacaagttg gaaactctga tggaaactca tgagcgtggt
1441 gtatctattc gccgacagtt actttccaag aagctttcag aaccttcttc tctccagtac
1501 ctaccttaca gggattataa ttactccttg gtgatgggag cttgttgtga aatgttatt
1561 ggatatatgc ccatccctgt tggagtggca ggaccccttt gcttagatga aaagaattt
1621 caggttccaa tggcaacaac agaaggttgt cttgtggcca gcaccaatag aggctgcaga
1681 gcaataggtc ttggtggagg tgccagcagc cgagtccttg cagatgggat gactcgtggc
1741 ccagttgtgc gtcttccacg tgcttgtgac tctgcagaag tgaaagcctg gctcgaaaca
1801 tctgaagggt tcgcagtgat aaaggaggca tttgacagca ctagcagatt tgcacgtcta
1861 cagaaacttc atacaagtat agctggacgc aacctttata tccgtttcca gtccaggtca
1921 ggggatgcca tggggatgaa catgatttca aagggtacag agaaagcact ttcaaaactt
1981 cacgagtatt tccctgaaat gcagattcta gccgttagtg gtaactattg tactgacaag
2041 aaacctgctg ctataaattg gatagaggga agaggaaaat ctgttgtttg tgaagctgtc
2101 attccagcca aggttgtcag agaagtatta aagactacca cagaggctat gattgaggtc
2161 aacattaaca agaatttagt gggctctgcc atggctggga gcataggagg ctacaacgcc
2221 catgcagcaa acattgtcac cgccatctac attgcctgtg gacaggatgc agcacagaat
2281 gttggtagtt caaactgtat tactttaatg gaagcaagtg gtcccacaaa tgaagattta
2341 tatatcagct gcaccatgcc atctatagag ataggaacgg tgggtggtgg gaccaaccta
2401 ctacctcagc aagcctgttt gcagatgcta ggtgttcaag gagcatgcaa agataatcct
2461 ggggaaaatg cccggcagct tgcccgaatt gtgtgtggga ccgtaatggc tggggaattg
2521 tcacttatgg cagcattggc agcaggacat cttgtcaaaa gtcacatgat tcacaacagg
2581 tcgaagatca atttacaaga cctccaagga gcttgcacca agaagacagc cggctcagga
2641 ggttcttcag gactggaagt gctgtttcag ggcccgggtg atctggcat gatgcctgaa
2701 ataaacacta accacctcga caagcaacag gttcaactcc tggcagagat gtgtatcctt
2761 attgatgaaa atgacaataa aattggagct gagaccaaga agaattgtca cctgaacgag
2821 aacattgaga aggattatt gcatcgagct tttagtgtct tcttattcaa caccgaaaat
2881 aagcttctgc tacagcaaag atcagatgct aagattacct ttccaggttg ttttacgaat
2941 acgtgttgta gtcatccatt aagcaatcca gccgagcttg aggaaagtga cgcccttgga
3001 gtgaggcgag cagcacagag acggctgaaa gctgagctag gaattccctt ggaagaggtt
3061 cctccagaag aaattaatta tttaacacga attcactaca agctcagtc tgatggtatc
3121 tggggtgaac atgaaattga ttacattttg ttggtgagga agaatgtaac tttgaatcca
3181 gatcccaatg agattaaaag ctattgttat gtgtcaaagg aagaactaaa agaacttctg
```

```
-continued
3241 aaaaaagcag ccagtggtga aattaagata acgccatggt ttaaaattat tgcagcgact 3301 tttctcttta aatggtggga taacttaaat catttgaatc agtttgttga ccatgagaaa 3361 atatacagaa tg
```

ERG2, ERG3, and ERG6 Mutations/Deletions for Increased Membrane Permeability

Same process as ERG9 knockout, but targeting ERG2, ERG3, and ERG6 genes.

ERG20p Modification

We experimented with a few types of ERG20 genes, (avian, salmon entrica, and human). Currently we are still trying to see which is the best by engineering the ERG20p gene into a FPP synthase, thereby creating a new enzyme that can create GPP instead at high rates.

Gal80p Deletion/Mutation for not Needing Expensive Galactose to Induce Promoter

Induce mutation in Gal80 gene by site directed mutagenesis.

Using ADH2p (Glucose Repressible Promoter) Induces Strong Transcription with No Glucose, Better than GAL Promoter Same process as Gal80p deletion.

Overexpression of ADH2 and ALD6 (Ethanol to Acetate), as Well as Overexpression of an Acetyl-CoA C-Acetyltransferase Same process as IDI and HMGR overexpression, but with genes for ADH2 and ALD6.

Tables

Below is a table of various cannabinoids, along with their structure and variants and main pharmacological characteristics as well as a table listing potential starting materials.

TABLE 1

| Compounds | Pharmacological Characteristics |
|---|---|
| Cannabinoids (FIG. 1 and 2) | |
| Cannabigerolic acid (CBGA) | Antibiotic (1) |
| Cannabigerolic acid monomethylether (CBGAM) | |
| Cannabigerol (CBG) | Antibiotic, antifungal, anti-inflammatory, analgesic (1) Partial agonist at CB1/CB2 receptors (2) |
| Cannabigerovarinic acid (CBGVA) | |
| Cannabigerovarin (CBGV) | |
| Cannabichromenic acid (CBCA) | |
| Cannabichromene (CBC) | Anti-inflammatory, antibiotic, antifungal, analgesic (1) |
| Cannabichromevarinic acid (CBCVA) | |
| Cannabichromevarin (CBCV) | |
| Cannabidiolic acid (CBDA) | Antibiotic |
| Cannabidiol (CBD) | Anxiolytic, antipsychotic, analgesic, anti-inflammatory, antioxidant, antispasmodic (1) Ant schizophrenic, antiepileptic, sleep-promoting, anti-oxidizing, anti-inflammatory, immunomodulation properties (2) |
| Cannabidiol monomethylether (CBDM) | |
| Cannabidiol-C4 (CBD-C4) | |
| Cannabidivarinic acid (CBDVA) | |
| Cannabidivarin (CBDV) | |
| Cannabidiorcol (CBD-C1) | |
| Tetrahydrocannabinolic acid A (THCA-A) | |
| Tetrahydrocannabinolic acid B (THCA-B) | |
| Delta-9-tetrahydrocannabinol (THC) | Euphoriant, analgesic, anti-inflammatory, antioxidant, antiemetic (1) |
| Delta-9-tetrahydrocannabinolic acid-C4 (THCA-C4) | |
| Delta-9-tetrahydrocannabinol-C4 (THC-C4) | |
| Delta-8-tetrahydrocannabivarin (D8-THCV) | Exhibit in vitro pharma properties similar to THCV, and both can antagonize THC; behave as agonists or antagonists in dose dependent manner (2) |
| Delta-9-tetrahydrocannabivarinic acid (THCVA) | |
| Delta-9-tetrahydrocannabivarin (THCV) | Analgesic, euphoriant (1) Strong antagonist of anandamide (due to interactions with non-CB1/2 receptors), neuromodulator (in animal and human organs), some affects due to interaction with non CB1/CB2 receptors (2) |
| Delta-9-tetrahydrocannabiorcolic acid (THCA-C1) | |
| Delta-9-tetrahydrocannabiorcol (THC-C1) | |
| Delta-7-cis-iso-tetrahydrocannabivarin (D7-THCV) | |
| Delta-8-tetrahydrocannabinolic acid (D8-THCA) | |
| Delta-8-tetrahydrocannabinol (D8-THC) | Similar to THC (1) Several 1-O-methyl- and 1-deoxy-delta-8-THC analogs have high |

TABLE 1-continued

| Compounds | Pharmacological Characteristics |
|---|---|
| | CB2 receptor affinity[JWH133, JWH359, trans-(6aR,10aR)-3-(1,1-dimethylhexyl)-1-O-methyl-delta-8-THC]; antiemetic effects similar to THC (2) |
| Cannabicyclolic acid (CBLA) | |
| Cannabicyclol (CBL) | |
| Cannabicyclovarin (CBLV) | |
| Cannabielsoic acid A (CBEA-A) | |
| Cannabielsoic acid B (CBEA-B) | |
| Cannabielsoin (CBE) | |
| Cannabinolic acid (CBNA) | |
| Cannabinol (CBN) | Sedative, antibiotic, anticonvulsant, anti-inflammatory (1) |
| Cannabinol methylether (CBNM) | |
| Cannabinol-C4 (CBN-C4) | |
| Cannabivarin (CBV) | |
| Cannabinol-C2 (CBN-C2) | |
| Cannabinol-C1 (CBN-C1) | |
| Cannabinodiol (CBND) | |
| Cannabinodivarin (CBVD) | |
| Cannabitriol (CBT) | |
| 10-Ethoxy-9-hydroxy-delta-6a-tetrahydrocannabinol | |
| 8,9-Dihydroxy-delta-6a-tetrahydrocannabinol | |
| Cannabitriolvarin (CBTV) | |
| Ethoxy-cannabitriolvarin (CBTVE) | |
| Dehydrocannabifuran (DCBF) | |
| Cannabifuran (CBF) | |
| Cannabichromanon (CBCN) | |
| Cannabicitran (CBT) | |
| 10-oxo-delta-6a-tetrahydrocannabinol (OTHC) | |
| Delta-9-cis-tetrahydrocannabinol (Cis-THC) | |
| 3,4,5,6-Tetrahydro-7-hydroxy-alpha-alpha-2-trimethyl-9-n-propyl-2,6-methano-2H-1-benzoxocin-5-methanol (OH-iso-HHCV) | |
| Cannabiripsol (CBR) | |
| Trihydroxy-delta-9-tetrahydrocannabinol (triOH-THC) | |
| Terpenes/Terpenoids | |
| Beta-Myrcene | Analgesic, anti-inflammatory, antibiotic, antimutagenic |
| d-Limonene | Immune potentiator, antidepressant, antimutagenic |
| Linalool | Sedative, antidepressant, anxiolytic, immune potentiator |
| Trans-Ocimene | |
| Beta-Pinene | |
| Alpha-Pinene | Anti-inflammatory, bronchodilator, stimulant, antibiotic, antineoplastic, AChE inhibitor |
| Beta-Caryophyllene | Anti-inflammatory, cytoprotective, antimalarial, CB2 agonist |
| Delta-3-Carene | |
| Pulegone | AChE inhibitor, sedative, antipyretic |
| Trans-gamma-Bisabolene | |
| Trans-alpha-Farnesene | |
| Beta-Fenchol | |
| Beta-Phellandrene | |
| Alpha-Humulene | |
| Guajol | |
| Alpha-Gualene | |
| Alpha-Eudesmol | |
| Terpinolene | |
| Alpha-Selinene | |
| Alpha-Terpineol | Sedative, antibiotic, AChE inhibitor, antioxidant, antimalarial |
| Fenchone | |
| Camphene | |
| Cis-Sabinene hydrate | |
| Cis-Ocimene | |
| Beta-Eudesmol | |
| Beta-Selinene | |
| Alpha-trans-Bergamolene | |
| Gamma-Eudesmol | |
| Borneol | |
| Cis-beta-Farnescene | |
| Gamma-Curcumene | |
| Cis-gamma-Bisabolene | |
| Alpha-Thujene | |
| Epi-alpha-Bisabolol | |
| Ipsdienol | |
| Alpha-Yiangene | |
| Beta-Elemene | |
| Alpha-cis-Bergamontene | |
| Gamma-Muurolene | |
| Alpha-Cadinene | |
| Alpha-Longipinene | |
| Caryophyllene oxide | |
| Spermidine Alkaloids (FIG. 6) | |
| (+)-Cannabisativine | |
| Palustridine | |
| Palustrine | |
| Spermidine | |
| Anhydrocannabisativine | |
| Phenolic Amides and Lignanamides (FIG. 5) | |
| N-trans-Feruloyltyramine | |
| N-p-Coumaroyltyramine | |
| N-trans-Caffeoyltyramine | |
| Grossamide | |
| Cannabisin-A | |
| Cannabisin-B | |
| Cannabisin-C | |
| Cannabisin-D | |
| Cannabisin-E | |

TABLE 1-continued

| Compounds | Pharmacological Characteristics |
|---|---|
| Cannabisin-F | |
| Cannabisin-G | |
| Phenylpropanoids and Flavonoids (FIG. 4) | |
| Apigenin | |
| Luteolin | |
| Kaempferol | |
| Quercetin | |
| Orientin | |
| Vitexin | |
| Cannflavin A | Inhibit prostaglandin E2 in human rheumatoid synovial cells |
| Cannflavin B | Inhibit prostaglandin E2 in human rheumatoid synovial cells |
| Stilbenoids (FIG. 3) | |
| Cannabispiran | |
| Isocannabispiran | |

TABLE 1-continued

| Compounds | Pharmacological Characteristics |
|---|---|
| Cannabistilbene-IIa | |
| Cannabistilbene-IIb | |
| Cannithrene-1 | |
| Cannithrene-2 | |
| Acetyl cannabispirol | |
| Alpha-cannabisporanol | |
| Canniprene | |
| Cannabispirone | |

Table 2 (Starting Materials)

| | | |
|---|---|---|
| Sugar based concentrates (High Fructose Corn Syrup, Molasses) | Hemicellulose | Glycerol |
| Glucose | Xylose | Whey |
| Sucrose | Methanol | Biodiesel |
| Cellulose | Lactic Acid | Citrate |
| Ethanol | Lignin | Fructose |
| Succinic Acid | Arabinose | Biofuels |
| Biomass | Saccharose | Starch based products |
| Agricultural residue | Water hyacinth | Aquatic biomass |

The invention claimed is:

1. An isolated codon-optimized nucleic acid sequence of SEQ ID NO: 34 comprising:
   a nucleotide sequence that is at least 95% identical to the nucleic acid sequence of SEQ ID NO: 34;
   an isolated codon-optimized nucleic acid sequence of nucleic acids 5841 to 8867 of SEQ ID NO: 34; and
   a nucleotide sequence that is at least 95% identical to the nucleic acids 5841 to 8867 of SEQ ID NO: 34;
   wherein the isolated codon-optimized nucleic acid sequence of SEQ ID NO: 34 is a modified gene inserted into a host organism and thereby increasing carbon flux towards a first pathway over a second pathway in the host organism, and the modified gene is obtained by at least one of:
   mutagenesis, gene knockout, overexpression, gene deletion, and promoter addition.

* * * * *